(12) United States Patent
Janaway et al.

(10) Patent No.: US 9,390,227 B2
(45) Date of Patent: Jul. 12, 2016

(54) VISUALIZATION TOOL FOR QPCR GENOTYPING DATA

(71) Applicant: LIFE TECHNOLOGIES CORPORATION, Carlsbad, CA (US)

(72) Inventors: Gordon A. Janaway, Carlsbad, CA (US); Evelyn Wing-Sim Chan, Carlsbad, CA (US)

(73) Assignee: Life Technologies Corporation, Carlsbad, CA (US)

( * ) Notice: Subject to any disclaimer, the term of this patent is extended or adjusted under 35 U.S.C. 154(b) by 234 days.

(21) Appl. No.: 14/063,940

(22) Filed: Oct. 25, 2013

(65) Prior Publication Data

US 2014/0053095 A1 Feb. 20, 2014

Related U.S. Application Data

(63) Continuation of application No. 13/083,476, filed on Apr. 8, 2011, now Pat. No. 8,572,506.

(60) Provisional application No. 61/322,749, filed on Apr. 9, 2010.

(51) Int. Cl.
*G06F 3/00* (2006.01)
*G06F 19/26* (2011.01)
*G06F 19/18* (2011.01)

(52) U.S. Cl.
CPC ............... *G06F 19/26* (2013.01); *G06F 19/18* (2013.01)

(58) Field of Classification Search
CPC .................................. G06F 19/26; G06F 19/18
USPC ........................................................ 715/771
See application file for complete search history.

(56) References Cited

U.S. PATENT DOCUMENTS

| 6,027,880 A | 2/2000 | Cronin et al. |
| 6,300,063 B1 | 10/2001 | Lipshutz et al. |
| 7,197,400 B2 * | 3/2007 | Liu .......... G06F 19/20 702/19 |

(Continued)

FOREIGN PATENT DOCUMENTS

| JP | 2007-049985 | 3/2007 |
| WO | 2009/086415 | 7/2009 |

OTHER PUBLICATIONS

International Search Report with the Written Opinion for International Application No. PCT/US2011/031855 dated Oct. 26, 2011.

(Continued)

*Primary Examiner* — David Phantana Angkool

(57) ABSTRACT

Systems and methods are used to display data obtained from a qPCR instrument. Each of two or more samples is probed with a first labeling probe and a second labeling probe. A first data set is received from a qPCR instrument at a first cycle number that includes for each sample a first labeling probe intensity, and a second labeling probe intensity. A second data set is received at a second cycle number that includes for each sample a first labeling probe intensity and a second labeling probe intensity. A first plot of first labeling probe intensity as a function of second labeling probe intensity is created using the first data set. A second plot of first labeling probe intensity as a function of second labeling probe intensity is created using the second data set. The first plot and the second plot are displayed in response to user defined input to provide dynamic and real-time analysis of genotyping data.

16 Claims, 18 Drawing Sheets

(56) References Cited

U.S. PATENT DOCUMENTS

| | | | |
|---|---|---|---|
| 7,991,564 B2 | 8/2011 | Huang et al. | |
| 8,030,094 B2 | 10/2011 | Walt et al. | |
| 8,095,323 B2 | 1/2012 | Lipshutz et al. | |
| 8,200,440 B2 * | 6/2012 | Hubbell | G06F 19/18 435/6.11 |
| 8,293,684 B2 | 10/2012 | Mouritzen et al. | |
| 8,572,506 B2 * | 10/2013 | Janaway | G06F 19/26 715/764 |
| 2005/0142599 A1 | 6/2005 | Shim et al. | |
| 2005/0255485 A1 * | 11/2005 | Livak | C12Q 1/6827 435/6.17 |
| 2005/0287575 A1 * | 12/2005 | Di | G06F 19/18 435/6.11 |
| 2006/0068377 A1 | 3/2006 | Tsipouras et al. | |
| 2006/0252059 A1 | 11/2006 | Kim et al. | |
| 2008/0120038 A1 * | 5/2008 | Ghosh | G06F 19/20 702/19 |
| 2008/0125979 A1 * | 5/2008 | Yakhini | G06F 19/20 702/20 |
| 2008/0287308 A1 | 11/2008 | Hubbell et al. | |
| 2009/0246777 A1 | 10/2009 | Shain | |
| 2011/0252353 A1 * | 10/2011 | Janaway | G06F 19/26 715/771 |

OTHER PUBLICATIONS

Johnson, Victor J. et al., "Genotyping of Single Nucleotide Polymorphism in Cytokine Genes Using Real-Time PCR Allelic Discrimination Technology", vol. 27, No. 6, 2004, 135-141.

* cited by examiner ed States Patent...

VISUALIZATION TOOL FOR QPCR GENOTYPING DATA

CROSS-REFERENCE TO RELATED APPLICATIONS

This application is a continuation of U.S. Non-Provisional application Ser. No. 13/083,476 filed Apr. 8, 2011, which claims priority to U.S. Provisional Application No. 61/322,749 filed Apr. 9, 2010, both of which are incorporated herein by reference.

INTRODUCTION

Quantitative polymerase chain reaction (qPCR) instruments or cyclers allow data to be collected during each cycle. PCR data is typically collected at each cycle using an optical system within the qPCR instrument that can detect electromagnetic radiation emitted by one or more labeling probes attached to each nucleic acid sample analyzed by the qPCR instrument. The PCR data, therefore, includes one or more labeling probe intensity values for each sample at each cycle or at each time associated with a cycle.

Various embodiments of systems according to the present teachings include a qPCR instrument, as well as a processor or computer for controlling and/or monitoring the qPCR instrument. The processor is used to create and modify the experiment parameters sent to the qPCR instrument and/or to monitor the qPCR instrument and analyze the PCR data received from the qPCR instrument after the experiment. Although qPCR systems receive and analyze the qPCR data, they generally only display useful or discriminatory information at the end-point or after completion of the PCR experiment. Also, although the qPCR instrument and the processor of a qPCR system can communicate across a network, each qPCR system may include one qPCR instrument and one processor. Finally, although high throughput experimental workflows may require that the same PCR experiment be run on batches of samples, qPCR systems may often require entry of experimental parameters for each batch placed in a qPCR instrument.

BRIEF DESCRIPTION OF THE DRAWINGS

The skilled artisan will understand that the drawings, described below, are for illustration purposes only. The drawings are not intended to limit the scope of the present teachings in any way.

DESCRIPTION OF VARIOUS EMBODIMENTS

Various embodiments of systems and methods of a visualization tool for qPCR genotyping data may provide an end user a dynamic display of genotyping data in response to end user input. The interactive nature of various embodiments of systems and methods of the present teachings allows an end user command of a significant amount of information displayed as a time-based plot of the data, which may be accessed in a step-wise fashion from user input, or may be accessed as a video display from user input. In various embodiments of systems and methods of a visualization tool for qPCR genotyping data, a sample table may be associated with the sample plot, which sample table may have a wide range of information associated with each sample represented in the table. In various embodiments of systems and methods of the present teachings, an end user may select a sample or samples represented on the sample table in any fashion desired; each sample having a wealth of sample information associated with it, and the selected sample or samples may be displayed on the plot of genotyping data. Accordingly, through such a visualization tool, an end user may dynamically understand the impact of a variety of experimental conditions on the outcome of a genotyping experiment. Such analysis may provide an end user with the ability to, for example, but not limited by, troubleshoot ambiguous endpoint data, make manual calls, enhance genotype assignment, optimize assay and analysis conditions.

Figure 1:
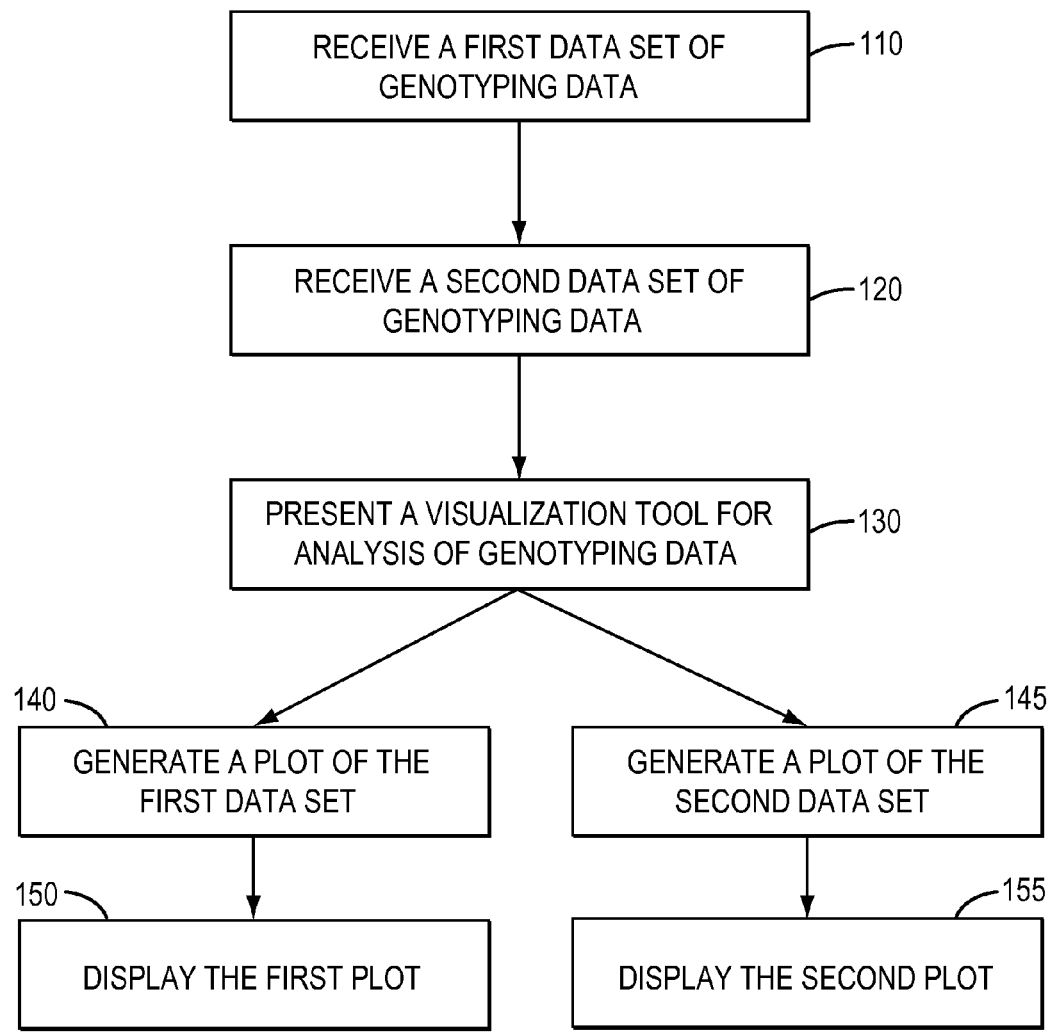
FIG. 1 is an exemplary flowchart showing a method for displaying data obtained from a qPCR instrument, upon which embodiments of the present teachings may be implemented.

FIG. 1 is a flow diagram depicting various embodiments of systems and methods of the present teachings for displaying and analyzing data from genotyping samples. As previously discussed, embodiments of systems on which embodiments of various methods may be implemented include qPCR instrument and processor, which may be in communication.

This communication can include the exchange of data or control information, for example.

As one of ordinary skill in the art is apprised, a PCR analysis is performed on a thermal cycling instrument, which has various protocols for cycling though a plurality of thermal cycles in order to amplify a gene target. In various embodiments of the present teachings, the number of cycles performed for the amplification may be between about 20-40 cycles. For various embodiments of the present teachings, the number of cycles performed for the amplification may be greater than 40 cycles. For amplification of a gene target a thermal cycling instrument may perform a first thermal cycle of a PCR experiment in a certain cycle time that may be associated with a first thermal cycle number.

In various embodiments of a genotyping analysis, two or more DNA samples are probed with a first probe and a second probe. As indicated in step 110 of FIG. 1, a processor may receive from a qPCR instrument based on any of a variety of protocols for data collection, a first data set at a first time that includes for each of the two or more DNA samples a first probe intensity and a second probe intensity at the first time. According to various embodiments of the present teachings, and as indicated in step 120 of FIG. 1, a processor may receive from a qPCR instrument based on any of a variety of protocols for data collection, a second data set at a second time that includes for each of the two or more DNA samples a first probe intensity and a second probe intensity at the second time.

According to various embodiments of the present teachings, a user interface may present to an end user a visualization tool for the analysis of the data sets received a first time and a second time. As previously mentioned, a plurality of samples may be processed for genotyping analysis in a batch, yielding data-intense data sets. Various embodiments of a systems and methods according to the present teachings provide for embodiments of a visualization tool that may assist an end user in the evaluation and analysis of such data-intense data sets. As indicated in step 140 of FIG. 1, for various embodiments of systems and methods according to the present teachings, in response to input from an end user, a processor may generate a first plot of first probe intensity versus a second probe intensity using the first data set. Further, as indicated by step 145 of FIG. 1, a processor may generate a second plot of first probe intensity as a function of second probe intensity using the second data set in response to input from an end user. As indicated in steps 150 and 155 of FIG. 1, according to various embodiments of systems and methods of the present teachings, a processor may display the first plot and the second plot in response to input from an end user. In various embodiments, the input may be an interactive process with a user interface to display the data in a step-wise fashion. In such embodiments, an end user may select any data set in any order for display. For various embodiments, input from an end user can include, for example, clicking on or using any icon in a graphical user interface, including but not limited to, a slider, scroll bar, knob, text box, and representation of a sample table. For various embodiments, the input may be a user selection to display the data as a video.

In various embodiments of systems and methods as indicated by FIG. 1, a processor may receive data during the run time of a PCR experiment. For example, a processor may receive the first data set from a qPCR instrument after the collection of the first data set and before collection of the second data set. Further, this protocol may be extended throughout the run time, so that, for example, a processor may receive the second data set from a qPCR instrument after the collection of the second data set and before collection of a subsequent data set.

According to various embodiments of systems and methods of the present teachings, a processor may receive the first data set and the second data set from a qPCR instrument after thermal cycling has completed. For example, a processor may receive the first data set and the second data set after it has been stored on a computer-readable medium.

According to various embodiments of systems and methods of the present teachings, as indicated in FIG. 1, in response to user input, a visualization tool may assist an end user in the displaying of various aspects of genotyping data sets, thereby facilitating in the analysis of genotyping data. In various embodiments, a processor may display a plot showing trajectory lines between the second data set and the first data set. In various embodiments, a processor may display on the first plot quality values for the first data set and displays on the second plot quality values for the second data set. According to various embodiments, a user interface provides an interaction between selections made on a sample table and dynamically displayed on a plot of genotyping data. In various embodiments, selections made by an end user from a user interface of a visualization tool may, for example, but not limited by, provide dynamic analysis for enabling an end user to, for example, but not limited by, troubleshoot ambiguous end-point data, make manual calls, use trajectory lines to assist in visualizing clusters to enhance genotype assignment, optimize assay conditions (i.e. labeling probe, assay buffer, etc.) and optimize analysis conditions.

Figure 6:
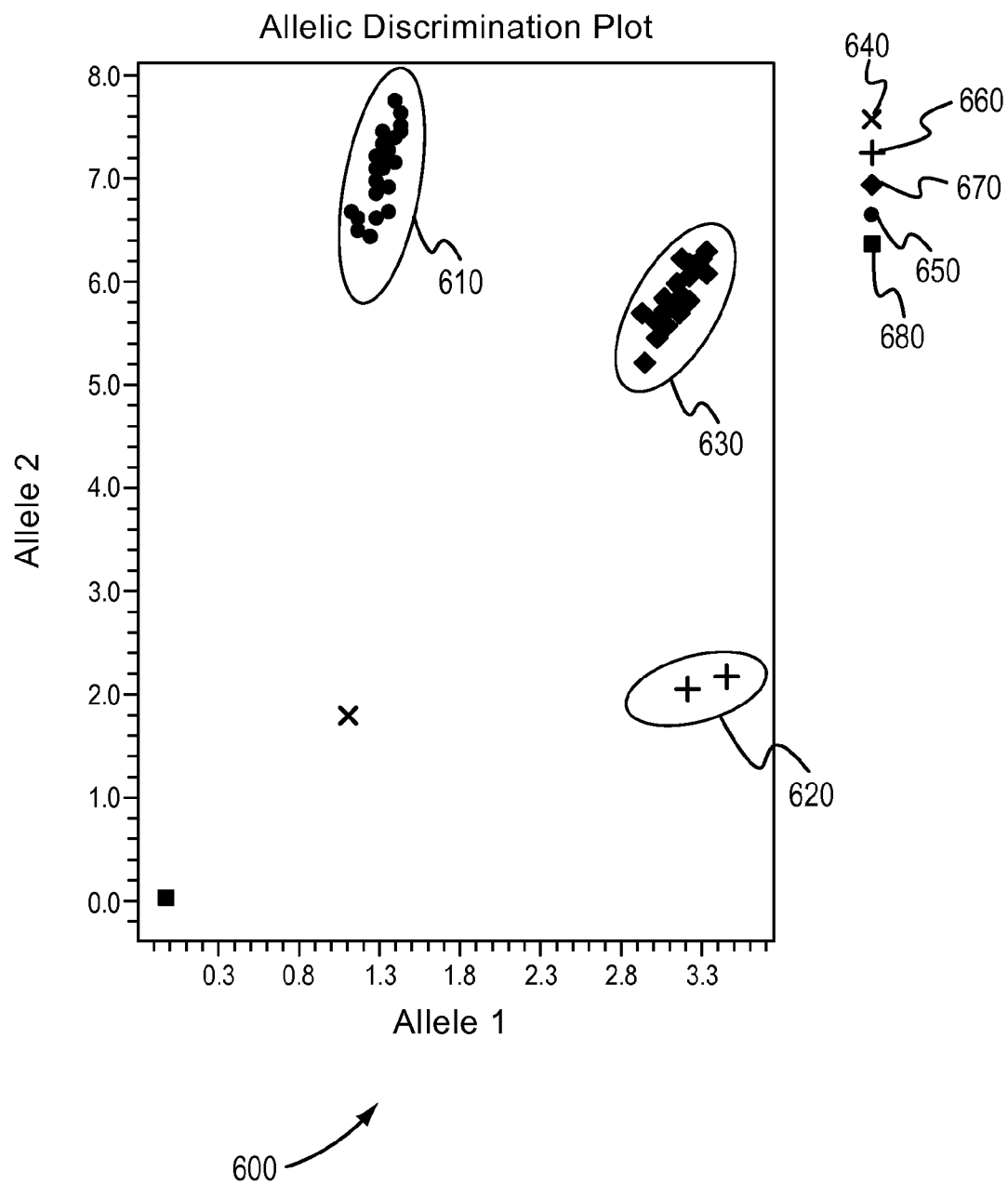
FIG. 6 is an exemplary allelic discrimination plot of end-point data where allelic discrimination is apparent, upon which embodiments of the present teachings may be implemented.

Various embodiments of methods and systems according to the present teachings may utilize data sets that may be represented, for example, but not limited by, according to the graph depicted in FIG. 6. Such a representation may arise from analyses utilizing two dyes having emissions at different wavelengths, which dyes can be associated with each of a labeling probe directed at one of two alleles for a genomic locus in a biological sample. In such duplex reactions, a discrete set of signals for each of three possible genotypes is produced. In a Cartesian coordinate system of signal 2 versus signal 1, as shown in FIG. 6, each data point shown on such a graphic representation may have coordinates in one of three discrete sets of signals given, for example in reference to FIG. 6, as (signal 2, signal 2), for which a cluster of data points 610 is displayed, (signal 2, signal 1) for which a cluster of data points 630 is displayed, and (signal 1, signal 1). for which a cluster of data points 620 is displayed. Accordingly, for each data point, a discrete set of signals for a plurality of samples may be stored as data points in a data set. Such data sets may be stored in a variety of computer readable media, and analyzed either dynamically during analysis or post analysis, as will be discussed in more detail subsequently.

One such type of assay used to demonstrate the features of embodiments of methods and systems for the visualization of genotyping data can utilize TaqMan® reagents, and may use, for example, but not limited by, FAM and VIC dye labels, as will be discussed subsequently. However, one of ordinary skill in the art will recognize that a variety of assays including labeling probe reagents may be utilized to produce data that may be analyzed according to various embodiments of methods and systems of the present teachings.

The term "labeling probe" generally, according to various embodiments, refers to a molecule used in an amplification reaction, typically for quantitative or qPCR analysis, as well as end-point analysis. Such labeling probes may be used to monitor the amplification of the target polynucleotide. In some embodiments, oligonucleotide labeling probes present in an amplification reaction are suitable for monitoring the amount of amplicon(s) produced as a function of time. Such oligonucleotide labeling probes include, but are not limited to, the 5'-exonuclease assay TaqMan® labeling probes described herein (see also U.S. Pat. No. 5,538,848), various stem-loop molecular beacons (see e.g., U.S. Pat. Nos. 6,103, 476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355,421 and 6,593,091), linear PNA beacons (see, e.g., Kubista et al., 2001, SPIE 4264:53-58), non-FRET labeling probes (see, e.g., U.S. Pat. No. 6,150,097), Sunrise®/Amplifluor® labeling probes (U.S. Pat. No. 6,548,250), stem-loop and duplex Scorpion™ labeling probes (Solinas et al., 2001, Nucleic Acids Research 29:E96 and U.S. Pat. No. 6,589,743), bulge loop labeling probes (U.S. Pat. No. 6,590, 091), pseudo knot labeling probes (U.S. Pat. No. 6,589,250), cyclicons (U.S. Pat. No. 6,383,752), MGB Eclipse™ probe (Epoch Biosciences), hairpin labeling probes (U.S. Pat. No. 6,596,490), peptide nucleic acid (PNA) light-up labeling probes, self-assembled nanoparticle labeling probes, and ferrocene-modified labeling probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Labeling probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Labeling probes can also comprise black hole quenchers (Biosearch), Iowa Black (IDT), QSY quencher (Molecular Labeling probes), and Dabsyl and Dabcel sulfonate/carboxylate Quenchers (Epoch). Labeling probes can also comprise two labeling probes, wherein for example a fluorophore is on one probe, and a quencher on the other, wherein hybridization of the two labeling probes together on a target quenches the signal, or wherein hybridization on target alters the signal signature via a change in fluorescence. Labeling probes can also comprise sulfonate derivatives of fluorescenin dyes with a sulfonic acid group instead of the carboxylate group, phosphoramidite forms of fluorescein, phosphoramidite forms of CY 5 (available for example from Amersham).

As used herein, the term "nucleic acid sample" refers to nucleic acid found in biological samples according to the present teachings. It is contemplated that samples may be collected invasively or noninvasively. The sample can be on, in, within, from or found in conjunction with a fiber, fabric, cigarette, chewing gum, adhesive material, soil or inanimate objects. "Sample" as used herein, is used in its broadest sense and refers to a sample containing a nucleic acid from which a gene target or target polynucleotide may be derived. A sample can comprise a cell, chromosomes isolated from a cell (e.g., a spread of metaphase chromosomes), genomic DNA, RNA, cDNA and the like. Samples can be of animal or vegetable origins encompassing any organism containing nucleic acid, including, but not limited to, plants, livestock, household pets, and human samples, and can be derived from a plurality of sources. These sources may include, but are not limited to, whole blood, hair, blood, urine, tissue biopsy, lymph, bone, bone marrow, tooth, amniotic fluid, hair, skin, semen, anal secretions, vaginal secretions, perspiration, saliva, buccal swabs, various environmental samples (for example, agricultural, water, and soil), research samples, purified samples, and lysed cells. It will be appreciated that nucleic acid samples containing target polynucleotide sequences can be isolated from samples using any of a variety of sample preparation procedures known in the art, for example, including the use of such procedures as mechanical force, sonication, restriction endonuclease cleavage, or any method known in the art.

The terms "target polynucleotide," "gene target" and the like as used herein are used interchangeably herein and refer to a particular nucleic acid sequence of interest. The "target" can be a polynucleotide sequence that is sought to be amplified and can exist in the presence of other nucleic acid molecules or within a larger nucleic acid molecule. The target polynucleotide can be obtained from any source, and can comprise any number of different compositional components. For example, the target can be nucleic acid (e.g. DNA or RNA). The target can be methylated, non-methylated, or both. Further, it will be appreciated that "target" used in the context of a particular nucleic acid sequence of interest additionally refers to surrogates thereof, for example amplification products, and native sequences. In some embodiments, a particular nucleic acid sequence of interest is a short DNA molecule derived from a degraded source, such as can be found in, for example, but not limited to, forensics samples. A particular nucleic acid sequence of interest of the present teachings can be derived from any of a number of organisms and sources, as recited above.

As used herein, "DNA" refers to deoxyribonucleic acid in its various forms as understood in the art, such as genomic DNA, cDNA, isolated nucleic acid molecules, vector DNA, and chromosomal DNA. "Nucleic acid" refers to DNA or RNA in any form. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA molecules. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, is generally substantially free of other cellular material or culture medium when produced by recombinant techniques, or free of chemical precursors or other chemicals when chemically synthesized.

Computer and Instrument Systems

Figure 2:
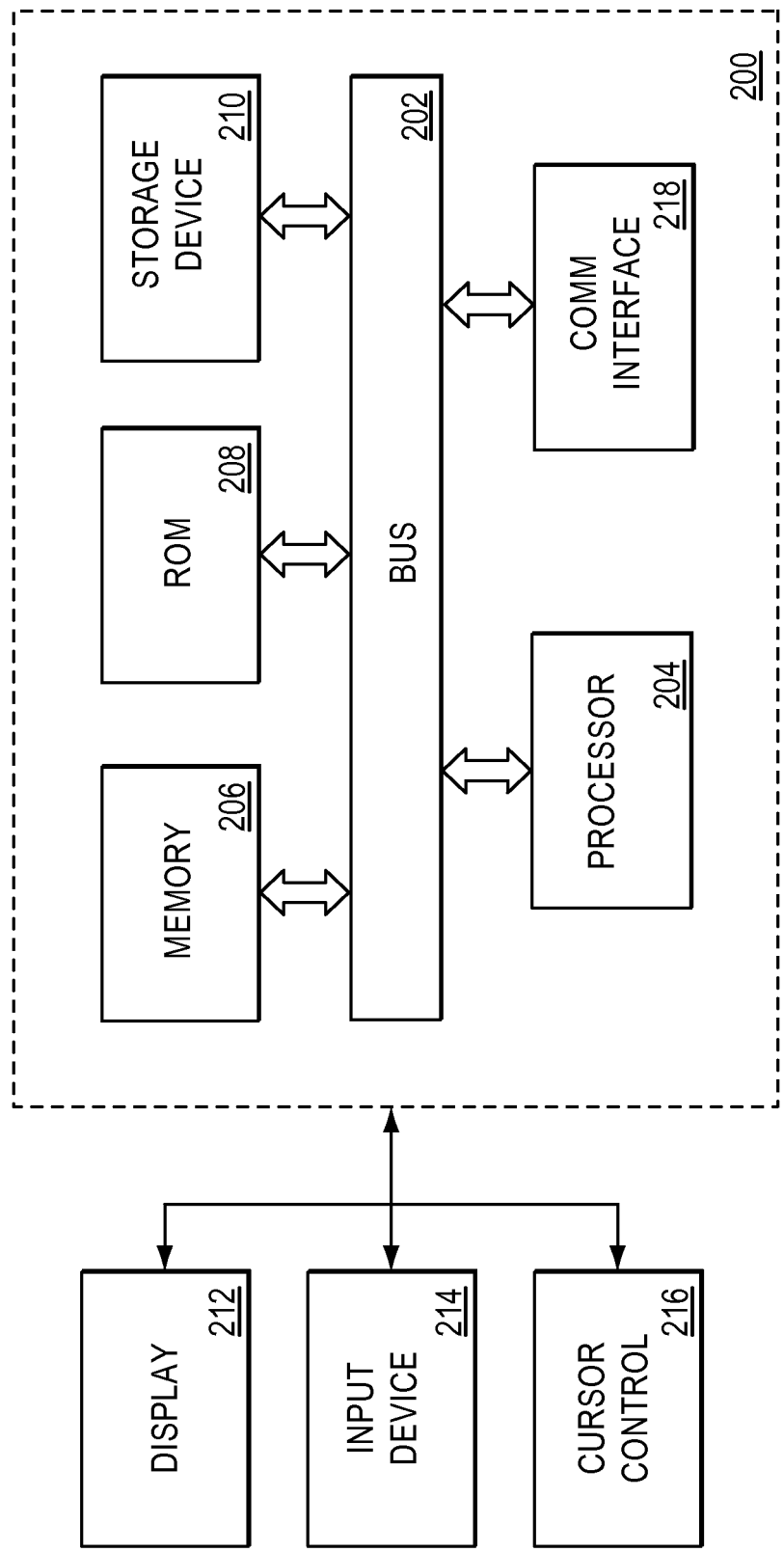
FIG. 2 is a block diagram that illustrates a polymerase chain reaction (PCR) instrument, upon which embodiments of the present teachings may be implemented.

Various embodiments of systems and methods for the analysis of genotyping data according to the present teachings may utilize various embodiments of a computer system depicted in the block diagrams shown in FIG. 2.

FIG. 2 is a block diagram that illustrates a computer system 200 that may be employed to carry out processing functionality, according to various embodiments, upon which embodiments of the present teachings may be implemented. Computing system 200 can include one or more processors, such as a processor 204. Processor 204 can be implemented using a general or special purpose processing engine such as, for example, a microprocessor, controller or other control logic. In this example, processor 204 is connected to a bus 202 or other communication medium.

Further, it should be appreciated that a computing system 200 of FIG. 2 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 200 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 200 may include bus 202 or other communication mechanism for communicating information, and processor 204 coupled with bus 202 for processing information.

Computing system 200 also includes a memory 206, which can be a random access memory (RAM) or other dynamic memory, coupled to bus 202 for storing instructions to be executed by processor 204. Memory 206 also may be used for storing temporary variables or other intermediate information during execution of instructions to be executed by processor 204. Computing system 200 further includes a read only memory (ROM) 208 or other static storage device coupled to bus 202 for storing static information and instructions for processor 204.

Computing system 200 may also include a storage device 210, such as a magnetic disk, optical disk, or solid state drive (SSD) are provided and coupled to bus 202 for storing information and instructions. Storage device 210 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, and/or data.

In alternative embodiments, storage device 210 may include other similar instrumentalities for allowing computer programs or other instructions or data to be loaded into computing system 200. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 210 to computing system 200.

Computing system 200 can also include a communications interface 218. Communications interface 218 can be used to allow software and data to be transferred between computing system 200 and external devices. Examples of communications interface 218 can include a modem, a network interface (such as an Ethernet or other NIC card), a communications port (such as for example, a USB port, a RS-232C serial port), a PCMCIA slot and card, Bluetooth, and the like. Software and data transferred via communications interface 218 are in the form of signals which can be electronic, electromagnetic, optical or other signals capable of being received by communications interface 218. These signals may be transmitted and received by communications interface 218 via a channel such as a wireless medium, wire or cable, fiber optics, or other communications medium. Some examples of a channel include a phone line, a cellular phone link, an RF link, a network interface, a local or wide area network, and other communications channels.

Computing system 200 may be in communication through communications interface 218 to a display 212, such as a cathode ray tube (CRT), liquid crystal display (LCD), and light-emitting diode (LED) display for displaying information to a computer user. In various embodiments, computing system 200, may be couple to a display through a bus. An input device 214, including alphanumeric and other keys, is coupled to bus 202 for communicating information and command selections to processor 204, for example. An input device may also be a display, such as an LCD display, configured with touch screen input capabilities. Another type of user input device is cursor control 216, such as a mouse, a trackball or cursor direction keys for communicating direction information and command selections to processor 204 and for controlling cursor movement on display 212. This input device typically has two degrees of freedom in two axes, a first axis (e.g., x) and a second axis (e.g., y), that allows the device to specify positions in a plane. A computing system 200 provides data processing and provides a level of confidence for such data. Consistent with certain implementations of embodiments of the present teachings, data processing and confidence values are provided by computing system 200 in response to processor 204 executing one or more sequences of one or more instructions contained in memory 206. Such instructions may be read into memory 206 from another computer-readable medium, such as storage device 210. Execution of the sequences of instructions contained in memory 206 causes processor 204 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 204 for execution. Such instructions, generally referred to as "computer program code" (which may be grouped in the form of computer programs or other groupings), when executed, enable the computing system 200 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 210. Volatile media includes dynamic memory, such as memory 206. Transmission media includes coaxial cables, copper wire, and fiber optics, including connectivity to bus 202.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 204 for execution. For example, the instructions may initially be carried on magnetic disk of a remote computer. The remote computer can load the instructions into its dynamic memory and send the instructions over a telephone line using a modem. A modem local to computing system 200 can receive the data on the telephone line and use an infra-red transmitter to convert the data to an infra-red signal. An infra-red detector coupled to bus 202 can receive the data carried in the infra-red signal and place the data on bus 202. Bus 202 carries the data to memory 206, from which processor 204 retrieves and executes the instructions. The instructions received by memory 206 may optionally be stored on storage device 210 either before or after execution by processor 204.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Figure 3:
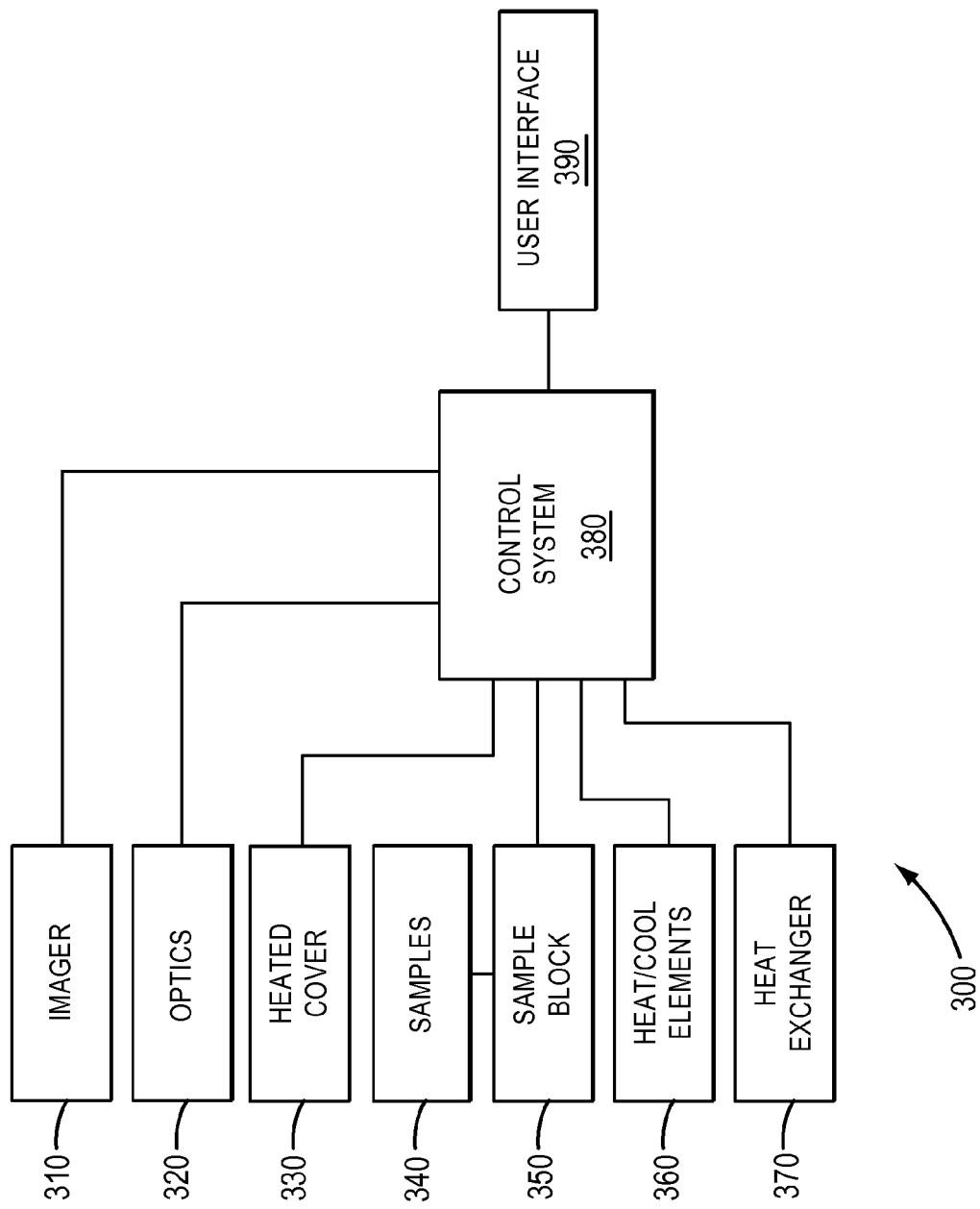
FIG. 3 is a block diagram that illustrates a computer system, upon which embodiments of the present teachings may be implemented.

Various embodiments of methods and systems for the analysis of genotyping data according to the present teachings may utilize various embodiments of a cycler instrument as depicted in the block diagram shown in FIG. 3.

FIG. 3 is a block diagram that illustrates a quantitative polymerase chain reaction (qPCR) instrument 300, upon which embodiments of the present teachings may be implemented. PCR instrument 300 may include a heated cover 330 that is placed over a plurality of samples 340 contained in a sample support device (not shown). In various embodiments, a sample support device may be a glass, metal or plastic slide with a plurality of sample regions, which sample regions have a cover between the sample regions and heated cover 330. Some examples of a sample support device may include, but are not limited to, a multi-well plate, such as a standard microtiter 96-well, a 384-well plate, a micro device capable of processing thousands of samples per analysis, such as various microfluidic devices, microcard devices, and micro chip devices. The sample regions in various embodiments of a sample support device may include depressions, indentations, holes, ridges, and combinations thereof, patterned in regular or irregular arrays formed on the surface of the substrate. Various embodiments of qPCR instruments include a sample block 350, elements for heating and cooling 360, a heat exchanger 370, control system 380, and user interface 390. In the present teachings, reference is made to end-point analysis. For PCR instrumentation dedicated to performing end-point analysis, detection is not done until the thermal cycling is completed. Such PCR instrumentation would generally not include imager 310 and optics 320.

For qPCR instrumentation depicted by FIG. 3, detection is performed during the run time of the analysis of biological samples. A detection system may have an illumination source (not shown) that emits electromagnetic energy, a detector or imager 310, for receiving electromagnetic energy from samples 340 in a sample support device, and optics 320 used to guide the electromagnetic energy from each sample to imager 310. For embodiments of PCR instrumentation according to the present teachings, control system 380 may be used to control the functions of the detection system, heated cover, and thermal block assembly. Control system 380 may be accessible to an end user through user interface 390. Also a computer system 200, as depicted in FIG. 2 may serve as to provide the control function to various PCR instrumentation according to the present teachings, as well as providing the user interface function. Additionally, computer system 200 of FIG. 2 may provide data processing, display and report preparation functions. All such instrument control functions may be dedicated locally to PCR instrumentation, or computer system 200 of FIG. 2 may provide remote control of part or all of the control, analysis, and reporting functions.

As previously mentioned, various embodiments of systems and methods according to the present teachings may have a computer in direct control and communication with a thermal cycling instrument. Various embodiments of methods and systems for the analysis of genotyping data according to the present teachings may utilize various embodiments of networking a thermal cycling instrument, as shown in FIG. 4.

Figure 4:
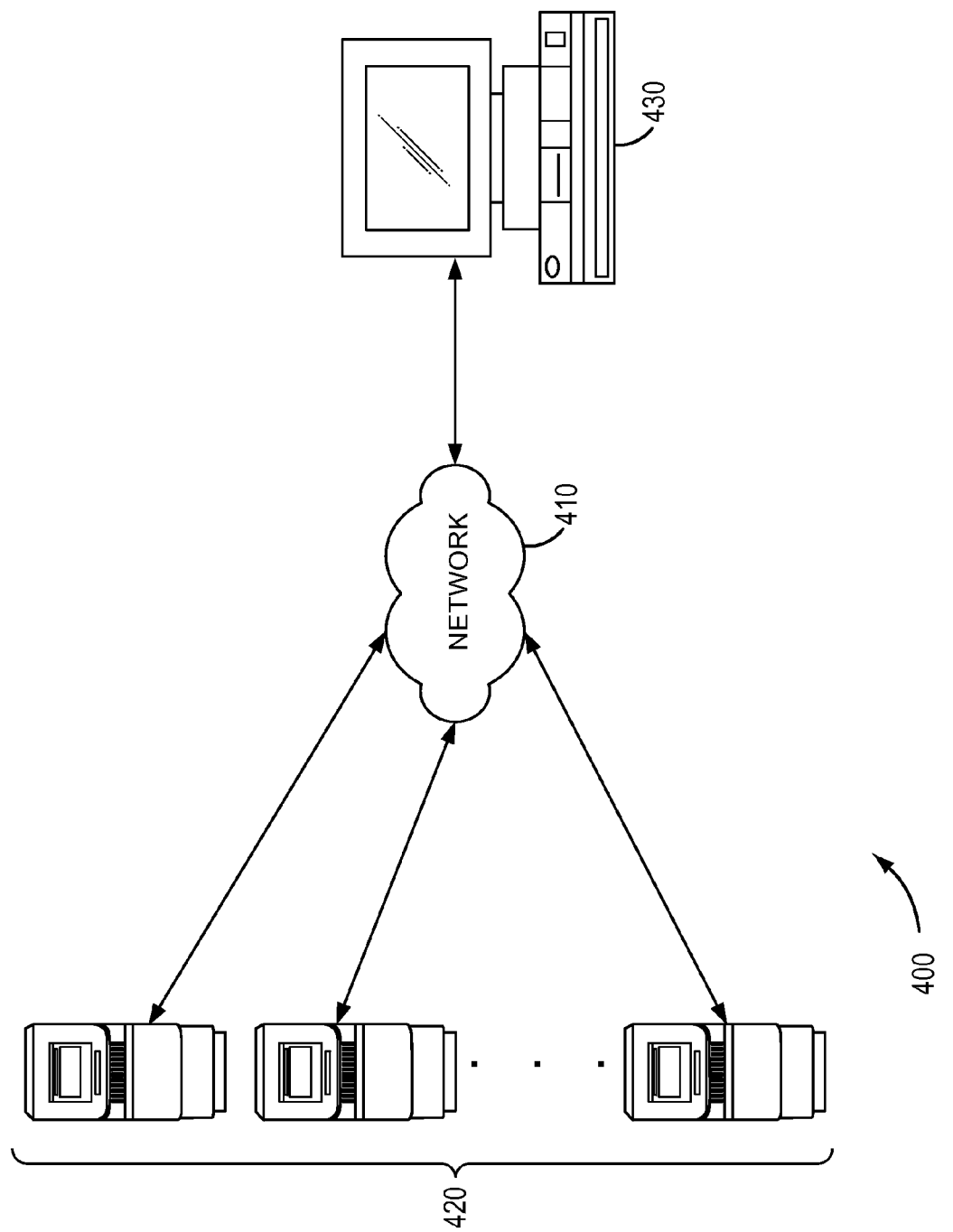
FIG. 4 is a diagram of a system for networking thermal cycling instruments, upon which embodiments of the present teachings may be implemented.

FIG. 4 is a diagram of a system 400 for networking qPCR instruments, upon which embodiments of the present teachings may be implemented. System 400 includes network 410, two or more qPCR instruments 420, and processor 430. The two or more qPCR instruments 420 and processor 430 are in communication. This communication can include the exchange of data or control information, for example.

Processor 430 can receive a labeling probe intensity from each of the two or more qPCR instruments 420. In other words, processor 430 can monitor two or more experiments from the two or more qPCR instruments 420 at substantially the same time. Communication between processor 430 and the two or more qPCR instruments 420 is not limited to PCR probe intensities, processor 430 can send and receive PCR experiment files used to control two or more qPCR instruments 420 and any data produced by the two or more qPCR instruments 420. FIG. 4 shows that system 400 provides a one-to-many relationship between processor 430 and the two or more qPCR instruments 420.

In various embodiments, system 400 provides a one-to-many relationship between one qPCR instrument and two or more processors (not shown). For example, system 400 allows one qPCR instrument to send the same measured probe intensity from a PCR experiment to two or more processors. In other words, system 400 allows one qPCR instrument to be monitored by two or more processors.

In various embodiments, processor 430 displays a listing of all PCR instruments connected to network 410. This listing can be used, for example, to select instruments to actively monitor. This listing can be displayed next to a window that shows the instruments currently being monitored. In various embodiments, during the creation of a PCR experiment, this listing may also be used to select the instrument on which the experiment will be conducted. Processor 430 creates an experiment for one or more of the two or more qPCR instruments 420 by creating a file that includes all of the parameters for the experiment. This file is then sent across network 410 to one of two or more qPCR instruments 420. The listing of all PCR instruments connected to the network is, for example, a pull down selectable list on a screen used to enter information for an experiment file.

In various embodiments, processor 430 displays a listing of the two or more PCR instruments it is actively monitoring. This listing may be used to select an instrument from which additional status information about a PCR experiment can be obtained.

In various embodiments, processor 430 can be used to create two or more experiments to be run on the same PCR instrument in a sequence. Such two or more experiments are batch experiments, for example. Batch experiments are created for a PCR instrument that includes, for example, a robotic arm that can load two or more sample plates sequentially. Processor 430 displays one or more selectable parameters that can be used to create two or more PCR experiments that are to be run in batch mode, for example. Alternatively, in various embodiments, processor 430 provides a command line interface that can be used to create two or more PCR experiments that are to be run in batch mode.

In various embodiments, processor 430 displays a selectable parameter that enables automatic export of data files from a PCR experiment. Typically a qPCR instrument stores the output data from an experiment on the PCR instrument. This output is then retrieved by accessing the qPCR instrument and requesting the data using a processor, such as processor 430. In batch processing throughput can be increased by instructing the qPCR instrument to automatically send output data at the end of an experiment to processor 430. The qPCR instrument can be instructed to export a file by placing a parameter in the experiment file created by processor 430, for example. In addition to requesting export of output data files, processor 430 can specify other parameters that include, but are not limited to, naming conventions for export files and locations on a storage medium where the output data should be sent. A naming convention can include adding a barcoded plate number to the output data file name, for example.

In various embodiments, processor 430 can display a window in which preferences for date, time, and numeric separation formats of data can be specified.

In various embodiments, processor 430 can display a window that allows a file that includes calibration information to be selected for a particular PCR experiment that is created.

In various embodiments, processor 430 can display for a gene expression experiment a selectable list of sample types, can display a selectable list of gene targets, and can plot threshold cycles of each selected gene target as function of sample type as a quality control.

While the above embodiments have been recited with respect to various embodiments of networked systems, one of ordinary skill in the art will recognize the applicability of the teachings to a single qPCR instrument in communication with a processor, memory, and display.

Visualization Tool: Dynamic Display of qPCR Data

As described above, although PCR systems receive and analyze data, they generally only display useful or discriminatory information at the end-point or after completion of the PCR experiment. For example, in quantitative PCR-based genotyping, intensity data can be obtained dynamically during runtime for two allele-specific labeling probes at each cycle. Traditionally, this qPCR data is viewed as an amplification plot. An amplification plot shows the intensities of one allele-specific labeling probe for a plurality of samples plotted against time, with intervals of cycle number, for the convenience to an end user. As one of ordinary skill in the art of cycle instrumentation is apprised, data may be collected from a detector using a variety of protocols, and is taken over time.

An amplification plot, however, does not generally show the extent of allelic discrimination.

Traditionally, the extent of allelic discrimination has been shown in allelic discrimination plots that use only end-point data. An allelic discrimination plot shows the intensities of a first allele-specific labeling probe for a plurality of samples plotted against the intensities of a second allele-specific labeling probe for the same plurality of samples, for example. The extent of allelic discrimination in allelic discrimination plots is shown as distances between clusters of data. Further, allelic discrimination plots can also show the results of clustering algorithms that call genotypes by labeling clusters with called allele values.

Figure 5:
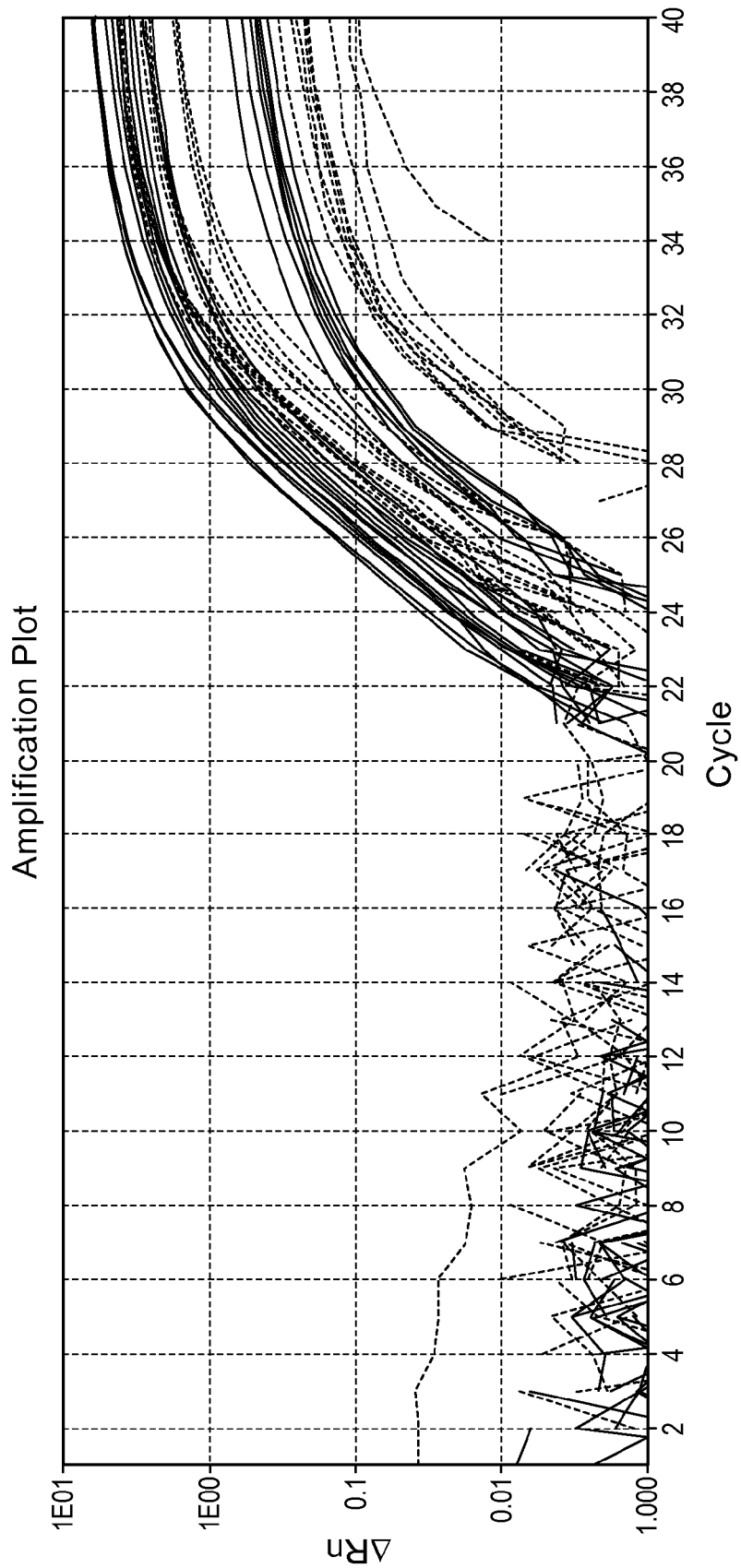
FIG. 5 is an exemplary amplification plot, upon which embodiments of the present teachings may be implemented.

FIG. 5 is an exemplary amplification plot 500, upon which embodiments of the present teachings may be implemented. The intensities shown in FIG. 5 are for the allele-specific labeling probe to provide for fluorescent detection, for example. Amplification of the allele-specific labeling probe for a large number of samples is apparent in plot 500. However, the extent of allelic discrimination is not apparent.

FIG. 6 is an exemplary allelic discrimination plot 600 of end-point data from the same experiment that produced the data of FIG. 5 where allelic discrimination is apparent, upon which embodiments of the present teachings may be implemented. The extent of allelic discrimination is apparent in plot 600 from the distances between clusters of data 610, 620, and 630. Further, the data shown in plot 600 was additionally processed so that the samples were specifically labeled as undetermined 640, first allele 650, second allele 660, both alleles 670, or no template control (NTC) 680 using a genotyping clustering algorithm, for example. Although the end-point data of plot 600 shows the extent of allelic discrimination, not all end-point data is guaranteed to show similar results.

Figure 7:
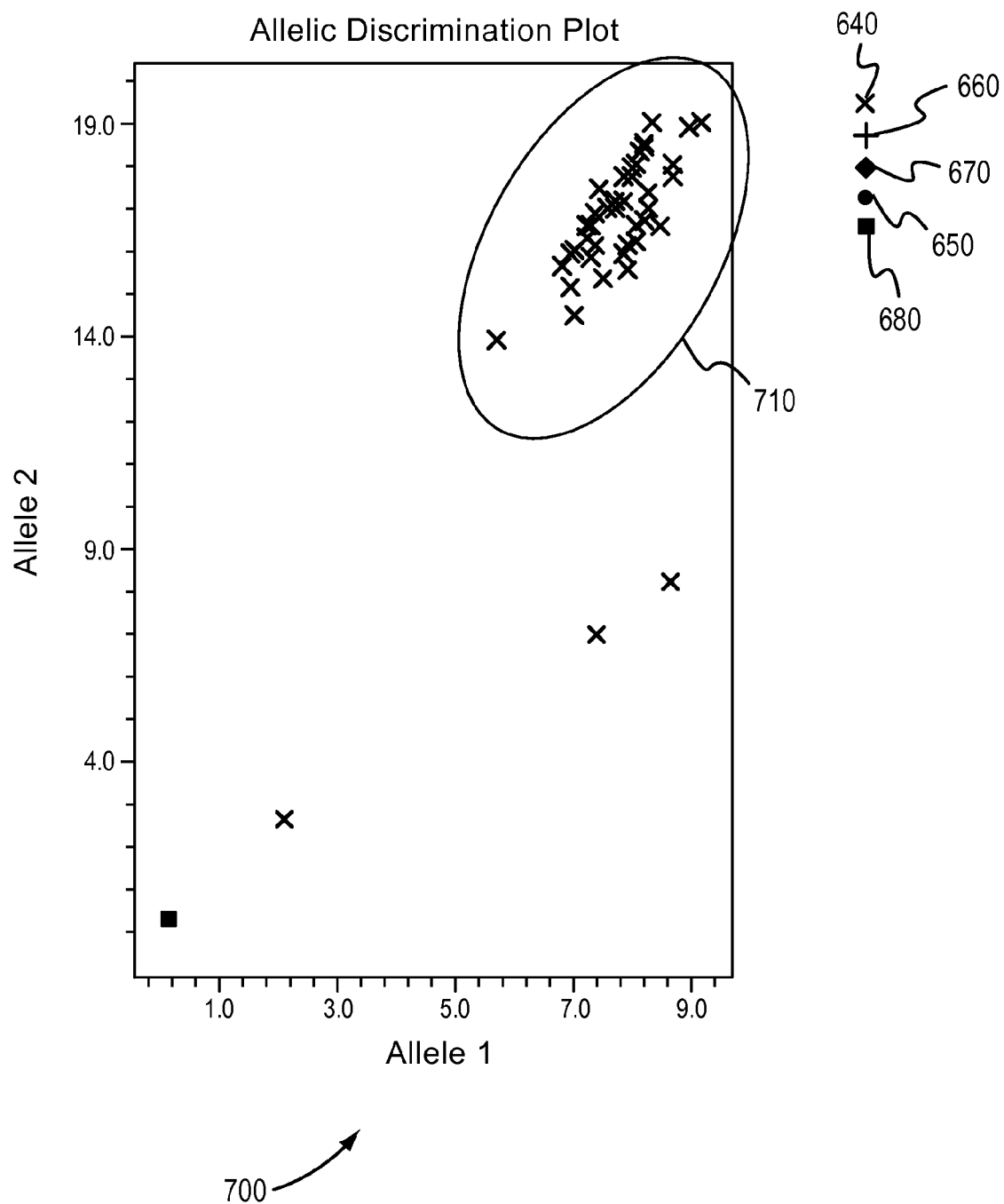
FIG. 7 is an exemplary allelic discrimination plot of end-point data where allelic discrimination is not apparent, upon which embodiments of the present teachings may be implemented.

FIG. 7 is an exemplary allelic discrimination plot 700 of end-point data from a different PCR experiment that used the same samples as were used to produce the data of FIG. 5 where allelic discrimination is not apparent, upon which embodiments of the present teachings may be implemented. The data of plot 700 of FIG. 7 and the data for plot 600 of FIG. 6 may be generated using different assay designs or different sample preparations, for example. Plot 700 of FIG. 7 shows little allelic discrimination and almost all sample values are located in one large area 710. In addition, a clustering algorithm labeled all data points of plot 700 as undetermined.

Figure 8:
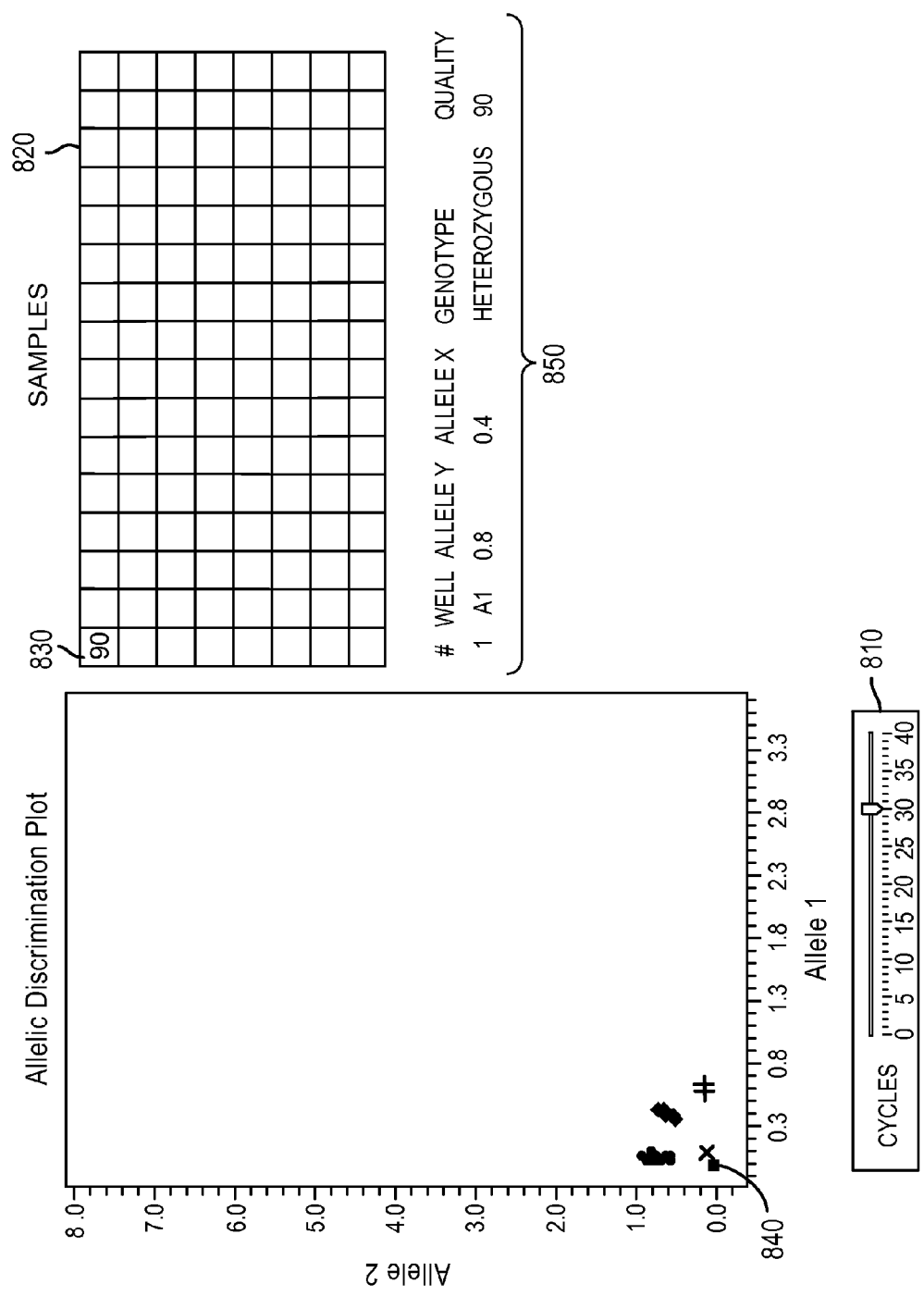
FIG. 8 is an exemplary allelic discrimination plot at cycle number 30 from the same experiment that produced the data of FIG. 6, upon which embodiments of the present teachings may be implemented.
Figure 9:
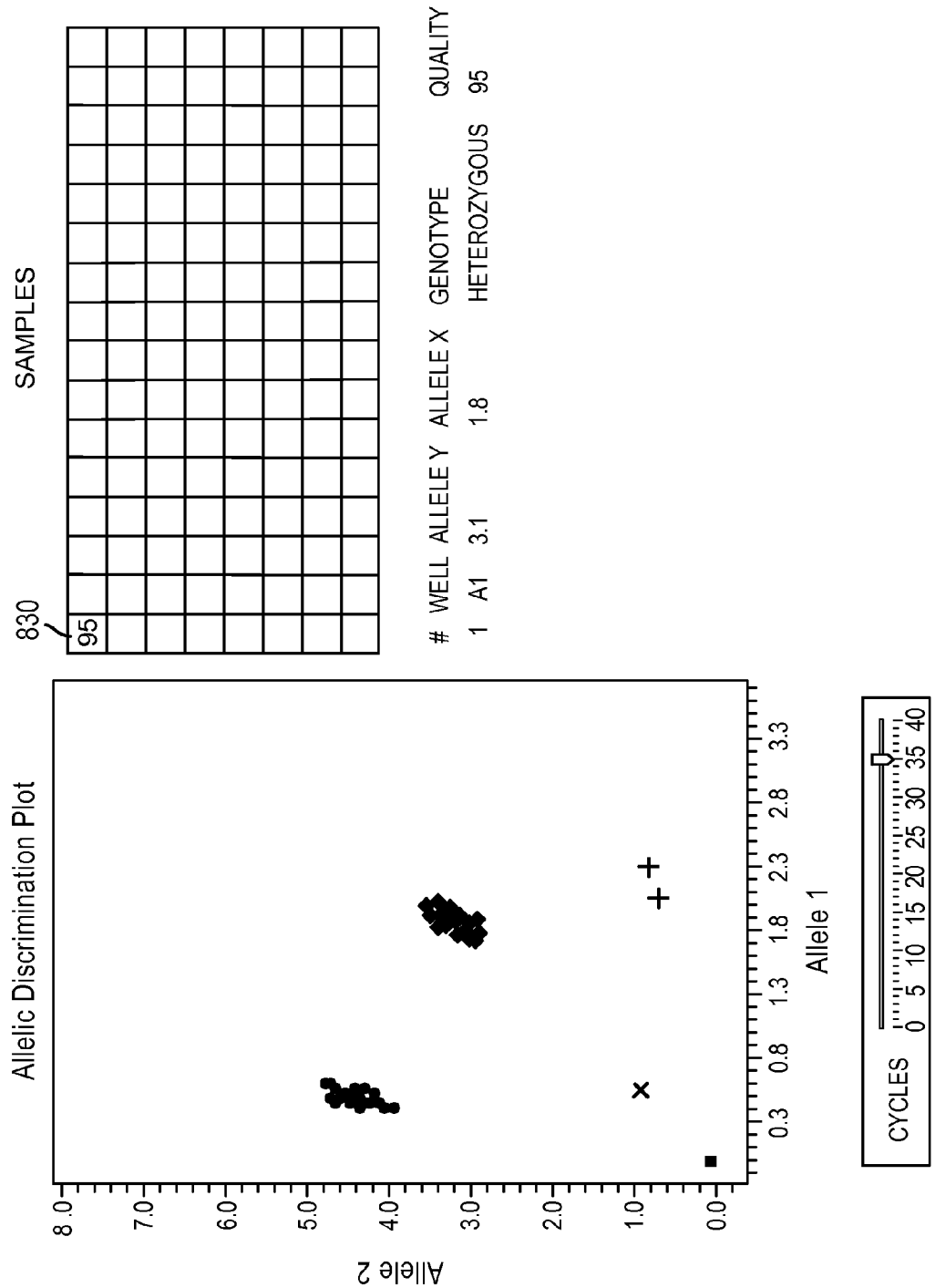
FIG. 9 is an exemplary allelic discrimination plot at cycle number 35 from the same experiment that produced the data of FIG. 6, upon which embodiments of the present teachings may be implemented.
Figure 10:
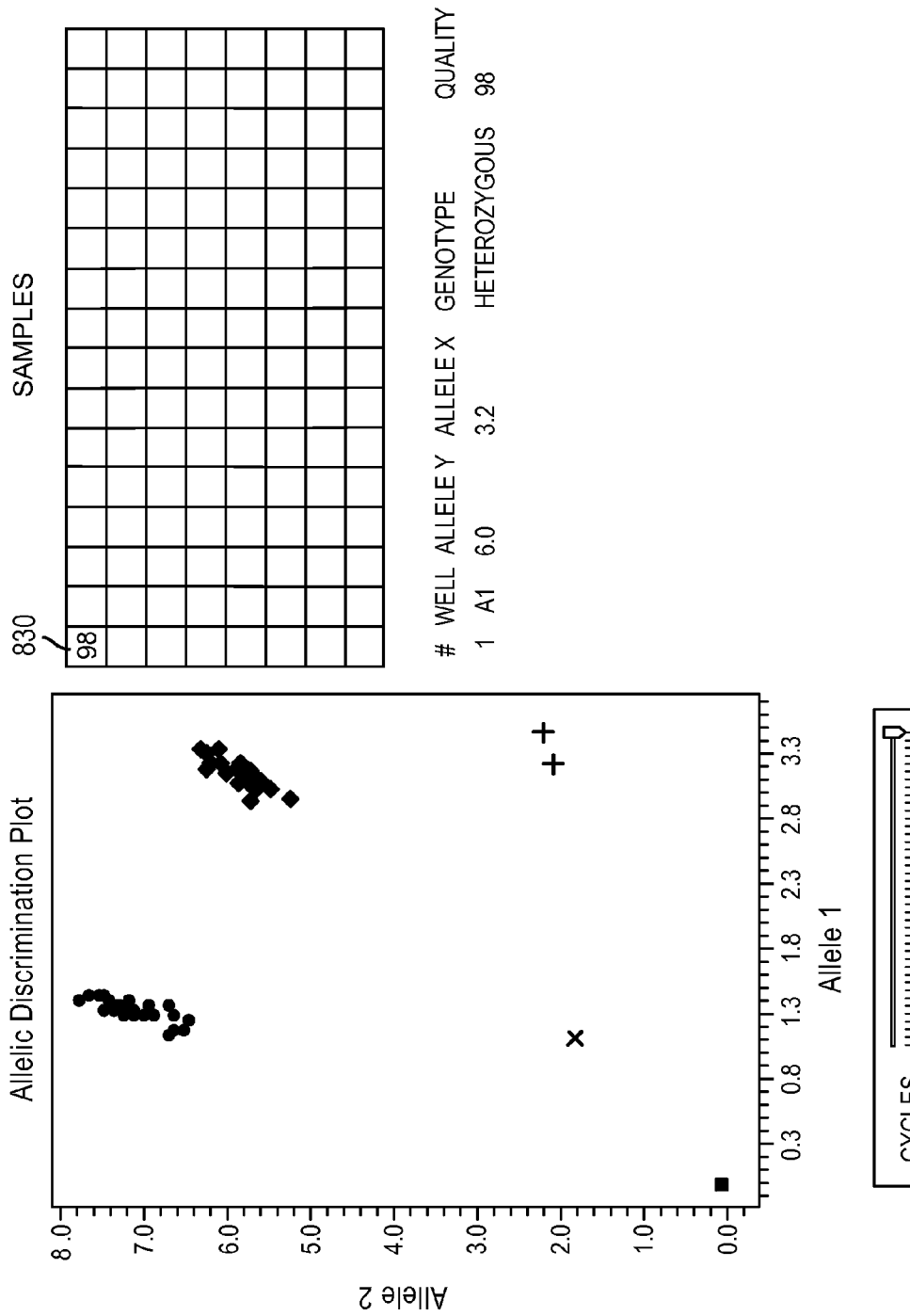
FIG. 10 is an exemplary allelic discrimination plot at cycle number 40 from the same experiment that produced the data of FIG. 6, upon which embodiments of the present teachings may be implemented.

According to various embodiments of the present teachings, the dimension of time shown in amplification plots, which is frequently displayed as cycle number, may be added to the allelic discrimination capability of allelic discrimination plots to increase the confidence of well discriminated results such as those shown in FIG. 6 or to troubleshoot undetermined results such as those shown in FIG. 7. Two or more allelic discrimination plots at corresponding two or more times may be displayed in succession to show the progression of allelic discrimination as a function of cycle number. These two or more allelic discrimination plots can be displayed under the control of a user in an interactive process provided by a user interface, or as a user selection to display the time-based data as a video, for example. These two or more allelic discrimination plots can be displayed dynamically during run time as the data is collected or after data collection from stored data. FIGS. 8-10 are three allelic discrimination plots corresponding to three different times during thermal cycling that show the progression of allelic discrimination as a function of cycle number. According to various embodiments of the present teachings, once the data has been stored, it may be reviewed at any time selected by a user. In various embodiments, time may be displayed as cycle number.

FIG. 8 is an exemplary allelic discrimination plot 800, according to various embodiments of the present teachings, which was produced using the data of FIG. 6. In FIG. 8, a graphical user interface according to the present teachings is shown presenting a user with a selection of time by selecting a cycle number; shown as cycle number 30. Plot 800 shows that at cycle number 30 the clusters of data are well-defined even though the distances between them are small.

Confidence or quality values for this data are also shown in plot 800. Sample table 820 provides a cell for each sample where a variety of information about the sample may be displayed, as will be discussed in more detail subsequently. In cell 830, for example, a confidence value of 90 percent is shown for a particular sample. Sample table 820 can include confidence values for all of the samples (not shown), for example. Plot 800 also includes a value for a blank or no template control (NTC) 840. According to various embodiments, an origin may be defined by a negative control. A negative control may be referred to as a non-template control (NTC), which is a sample not containing the target genomic locus of interest. For various embodiments of a genotyping assay, the negative control or NTC may contain no oligonucleotide material, and may contain, for example, but not limited by, all the reagents brought to a volume equal to biological samples being assayed. According to other embodiments of a genotyping assay, the NTC may contain, for example, but not limited by, an oligonucleotide sample validated not to contain the sequences of a target genomic locus being assayed. As one of ordinary skill in the art is apprised, such NTC samples may still produce a background signal that may be detected. In that regard, one or more NTC samples may be used to define an origin as well as a baseline from which the angles of the samples emitting a discrete set of signals for each of three possible allelic can be determined. In various embodiments, a plurality of NTC samples may be used to determine an origin and a baseline thereby. As one of ordinary skill in the art is apprised, there may be a variety of ways to process the data from a plurality of NTC samples to determine a value for the origin, including, but not limited by, the determination of the mean, the median, and the centroid of a plurality of NTC samples. NTC 840 is used to confirm that no intensity is found if no sample is present.

Confidence or quality values can also be displayed a part of a listing of information. Line 850 shows a confidence or quality value of 90 percent listing along with the well label, intensity values for each allele, and the genotype call. Lines can be displayed for all of the samples (not shown), for example.

FIG. 9 is an exemplary allelic discrimination plot 900 at cycle number 35 from the same experiment that produced the data of FIG. 6, upon which embodiments of the present teachings may be implemented. Plot 900 shows that at cycle number 35 the clusters of data are still well-defined and the distances between clusters are growing. The confidence value for the sample shown in cell 830 is even higher.

FIG. 10 is an exemplary allelic discrimination plot 1000 at cycle number 40 from the same experiment that produced the data of FIG. 6, upon which embodiments of the present teachings may be implemented. Plot 1000 shows that at cycle number 40 the clusters of data are again still well-defined and the distances between clusters have grown even more. The confidence value for the sample shown in cell 830 is again even higher.

FIGS. 8-10 show that displaying two or more allelic discrimination plots in response to input from an end user can provide additional information and enable a number of additional or alternative processing steps. For example, FIGS. 8-10 provide confidence to a user that the end-point data shown in FIG. 6 is correct.

Also, the well-defined clusters and high confidence values shown throughout the progress of reaction may suggest that the PCR experiment of FIGS. 6 and 8-10 may yield reliable results with less than the typically run 40 cycles; for example as few as 30 or 35 cycles. Therefore, certain assays for genotype discrimination can be modified and improved by viewing two or more allelic discrimination plots as a function of time. In various embodiments, if good results with high confidence are recognized by the PCR system as it is thermal cycling, it can stop the run and call the genotypes. This automatic step can increase experiment throughput by decreasing the thermal cycling time based on the qPCR data.

Additionally, the examples shown in FIGS. 8-10 include allelic labels generated by a genotyping algorithm. In various embodiments, two or more allelic discrimination plots can be displayed as a function of time, and do not include information from a genotyping algorithm. As a result, analyzing the data using various embodiments of the present teachings may provide an end user an ability to call the genotype manually. For example, by using displayed information, such as the well-defined clusters, the distances between clusters, and the confidence values, may provide an end user with sufficient information to make genotype calls.

Finally, in one traditional genotyping workflow the intensities of allele-specific labeling probes for each sample are read using a qPCR instrument before any thermal cycling is performed, which is often referred to as pre-read data acquisition. The samples are then cycled for a fixed number of cycles on a PCR instrument that does not include the capability of reading the intensities of allele-specific labeling probes of the samples. After the fixed number of cycles, the samples are returned to the qPCR system and a post-read or end-point data acquisition is performed. The genotype can be called in such a workflow by comparing allelic discrimination plots of the post-read and pre-read acquisitions. In various embodiments, displaying two or more allelic discrimination plots from a qPCR system can eliminate the need for post-read and pre-read acquisitions in a genotyping workflow. The two or more allelic discrimination plots can provide enough information to call the genotype.

FIGS. 8-10 show the progression of allelic discrimination as a function of cycle number over three separate plots. In various embodiments, information provided in these three separate plots can be assembled and displayed in one plot. For example, the data of FIGS. 8-10 can be plotted on one allelic discrimination plot and lines can be drawn between the different cycle number values. These lines may be referred to as trajectory lines.

Figure 11:
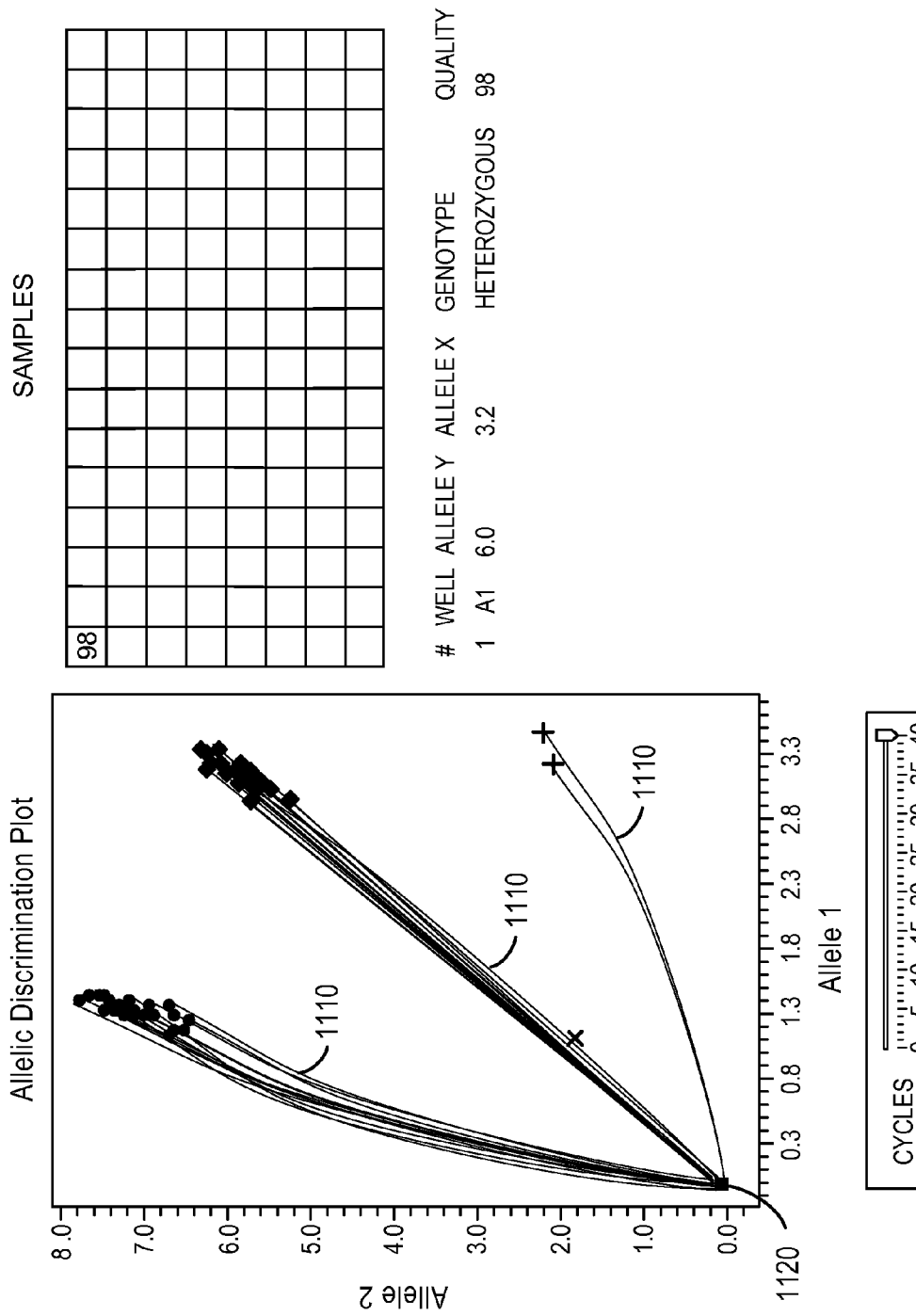
FIG. 11 is an exemplary allelic discrimination plot at cycle number 40 from the same experiment that produced the data of FIG. 6 showing trajectory lines representing data from previous cycle numbers, upon which embodiments of the present teachings may be implemented.

FIG. 11 is an exemplary allelic discrimination plot 1100 at cycle number 40 from the same experiment that produced the data of FIG. 5 showing trajectory lines 1110 representing data from previous cycle numbers, upon which embodiments of the present teachings may be implemented. Trajectory lines 1110 show the progression of allelic discrimination over cycle number. In various embodiments, trajectory lines 1110 can be added to or removed from plot 1000 under user control, for example.

The data in plot 1100 is shown in Cartesian coordinates. In various embodiments, this data can be plotted in polar coordinates. Polar coordinates are more relevant to some clustering algorithms, for example.

Trajectory lines 1110 converge to the data of the first cycle number at origin 1120. This convergence suggests that little or no intensities are observed at the beginning of thermal cycling. Traditionally, similar information has been provided by adding a blanks or NTCs to a plate well. Therefore, in various embodiments, providing trajectory lines for early cycle numbers can eliminate the need for blanks or NTCs. Eliminating blanks or NTCs increases the space on a plate for samples and can, therefore, increase experiment throughput.

Plot 1100 shows results from looking at one particular site on a genome. In various embodiments, plot 1100 can display data resulting from the analysis of two or more sites on the genome. This data is called multiplexed data, for example. The trajectories of the data from each site on the genome can have a different origin, for example. The trajectories of the data from each site on the genome can also have a different scale of intensity.

A clustering algorithm was run on the data shown in FIGS. 8-10 before the data was displayed. As described above, depending on the confidence at each cycle number for which data is displayed, the genotypes can be called. Similarly, in various embodiments, the trajectories of an allelic discrimination plot can be clustered into groups and these groups can be used to call genotypes. A hybrid recursive matching (HRM) algorithm can be used for example.

Generally, a clustering algorithm requires a certain number of samples clustered together to be able to call genotypes. For example, in single-nucleotide polymorphism (SNP) genotyping, 24 samples can be required for a given assay to cluster the samples into two homozygous clusters and one heterozygous cluster. In various embodiments, genotypes can be called from a single trajectory. For example, a trajectory that moves straight and then bends to the right can be called homozygous to a first allele, a trajectory that moves straight and then bends to the left can be called homozygous to a second allele, and a trajectory that does not curve can be called heterozygous. This type of trajectory pattern recognition can eliminate the need for data clustering algorithms.

In various embodiments, analyzing the trajectories of allelic discrimination plots can be used to rescue rare SNPs. With a rare SNP, almost all trajectories are homozygous. As a result, sample values are close together and a clustering algorithm has no basis to call the cluster. Trajectory lines, however, show that all data points started at the same point and migrated in one direction. As a result, the genotype can be called from the trajectory lines.

In various embodiments, plots showing the progression of allelic discrimination can be used to troubleshoot undetermined results or rescue precious samples. FIG. 7 is an allelic discrimination plot of end-point data that provides undetermined results. However, because FIG. 6 is plotted from same samples used in FIG. 5, it is known that genotyping these samples is possible.

Figure 12:
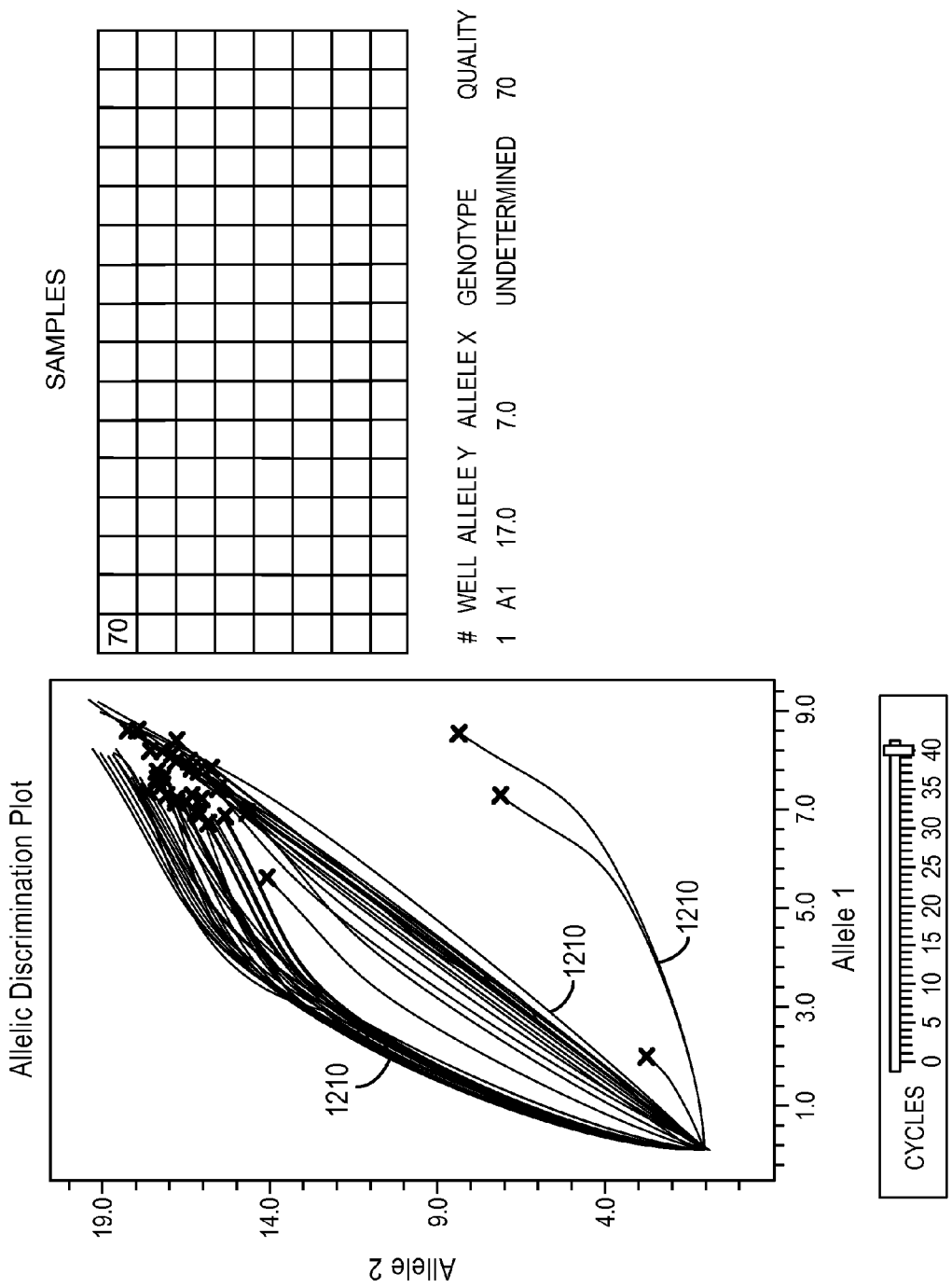
FIG. 12 is an exemplary allelic discrimination plot at cycle number 40 from the same experiment that produced the data of FIG. 7 showing trajectory lines representing data from previous cycle numbers, upon which embodiments of the present teachings may be implemented.

FIG. 12 is an exemplary allelic discrimination plot 1200 at cycle number 40 from the same experiment that produced the data of FIG. 6 showing trajectory lines 1210 representing data from previous cycle numbers, upon which embodiments of the present teachings may be implemented. Trajectory lines 1210 show that three clusters did separate at earlier cycle numbers. Trajectory lines 1210 can, therefore, be used to troubleshoot the data of FIG. 7. If the data of FIG. 7 is created from precious samples, trajectory lines 1210 of FIG. 12 can be used to rescue the data. Precious samples are samples that provide very small sample input. Precious samples include sample input from forensics, a few cells, or laser capture micro-dissection, for example. In various embodiments, trajectory lines 1210 are used to rescue the data from a precious sample by allowing the selection of a cycle number were the data was of sufficient quality to allow genotypes to be called. The data at this cycle number is then used to call the genotypes.

FIG. 12 shows that clusters of data separate during thermal cycling and then converge again near the end. Without showing the progression of allelic discrimination over cycle number, the separation and convergence are not apparent. In various embodiments, a PCR system can automatically monitor separation and convergence during a PCR run. If, for example, a transition from separation to convergence is found, the PCR system can adjust the thermal cycling to increase separation. For example, a PCR system can increase the annealing temperature.

In various embodiments of systems and methods according to the present teachings, a user interface providing dynamic display of genotyping data includes features providing the interaction between a sample table and a plot of genotyping data. In various embodiments, such a sample table may have a wide range of information associated with each sample represented in the table. According to various embodiments, the information may relate to a wide range of attributes associated with each sample. In various embodiment, such sample attributes can include, but are not limited to, sample, biological group, target, task, input quantity, time, time unit, sample source, treatment, and comments by an end user. For various embodiments, the information associated with each sample in a sample table may be related to a protocol under which the sample was run on a qPCR instrument. In various embodiments of systems and methods of the present teachings, an end user may select a sample or samples represented on the sample table in any fashion desired; each sample having a wealth of sample information associated with it, and the selected sample or samples may be displayed on the plot of genotyping data. According to various embodiments, an end user may scroll over samples entered in the sample table, and view the information related to each sample. In that regard, through such a visualization tool, an end user may dynamically understand the impact of a variety of experimental conditions on the outcome of a genotyping experiment.

Figure 13A:
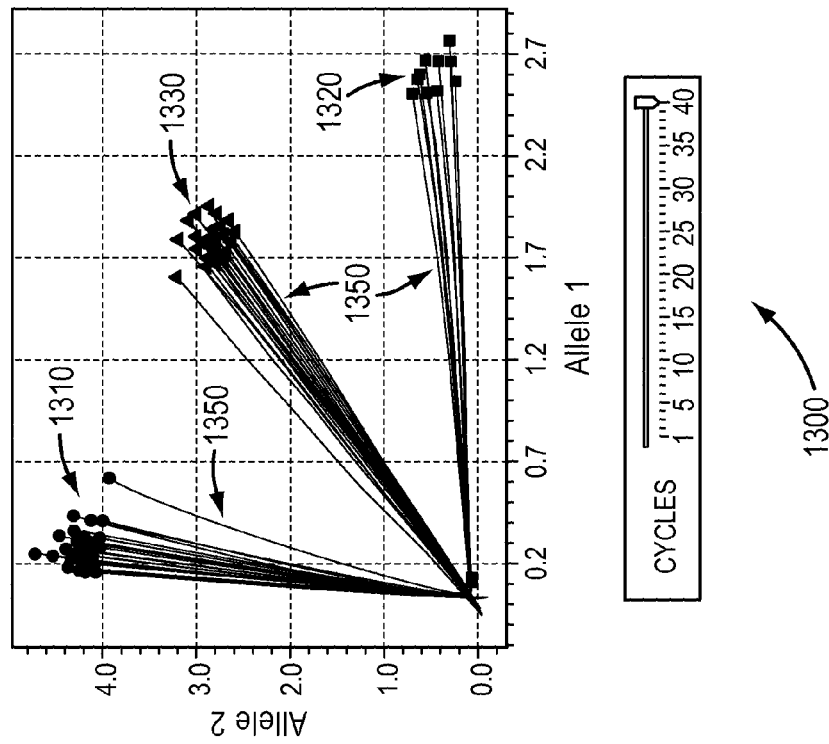
FIGS. 13A-13C display the interactive nature of an exemplary user interface, according to various embodiments of the present teachings.
Figure 13B:
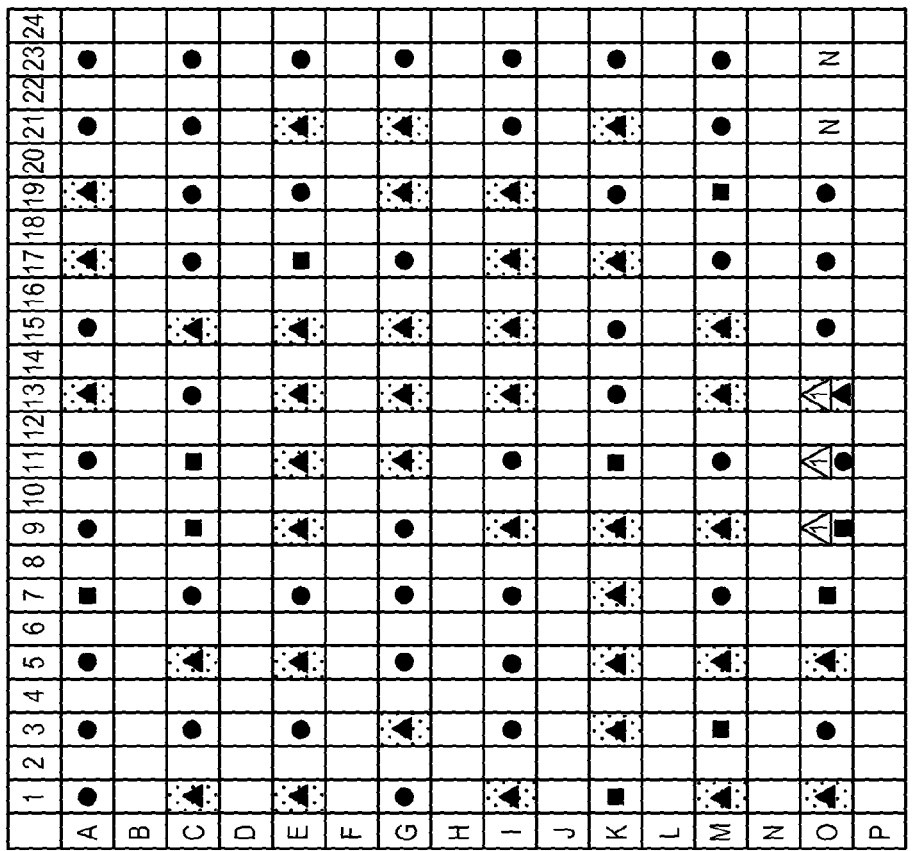
Figure 13B:
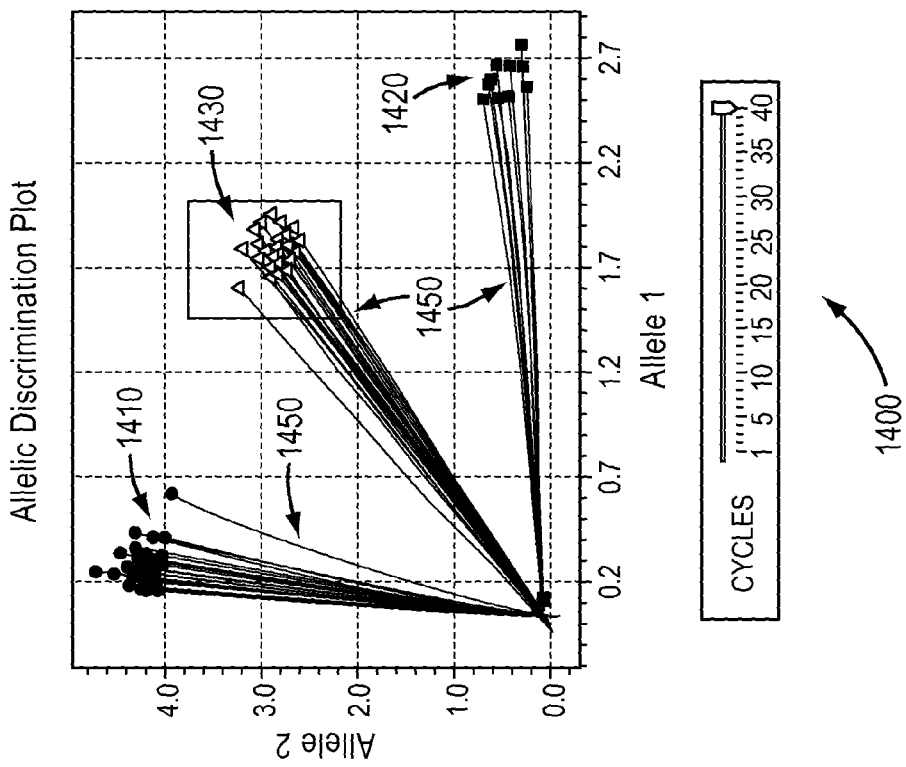
Figure 13C:
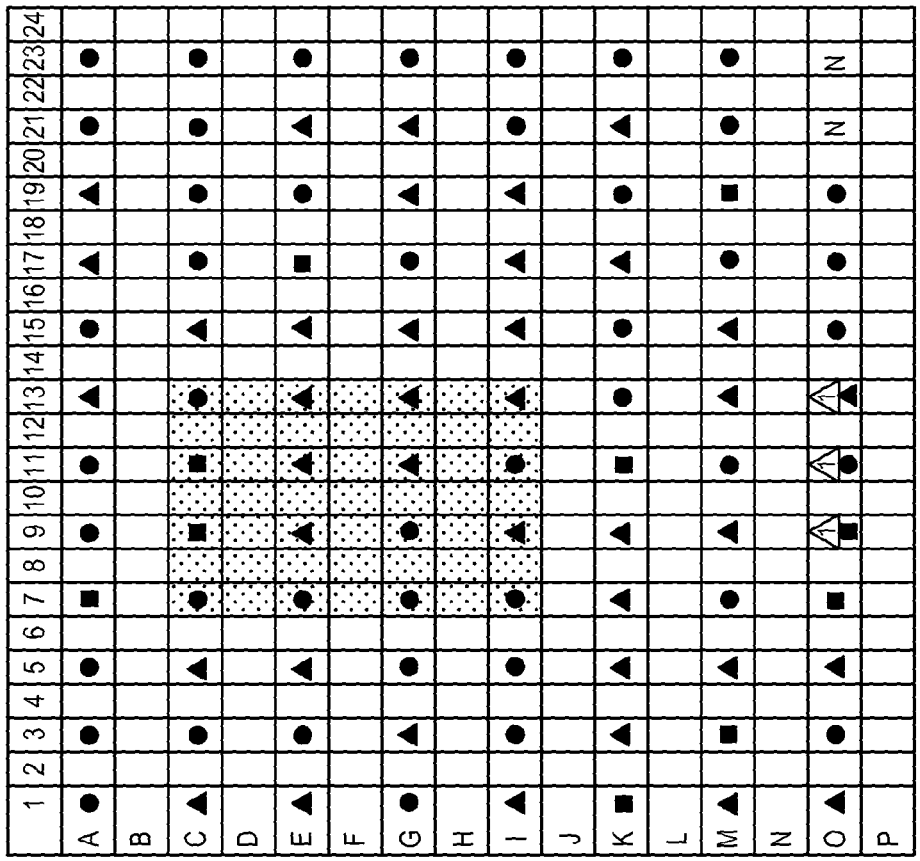
Figure 13C:
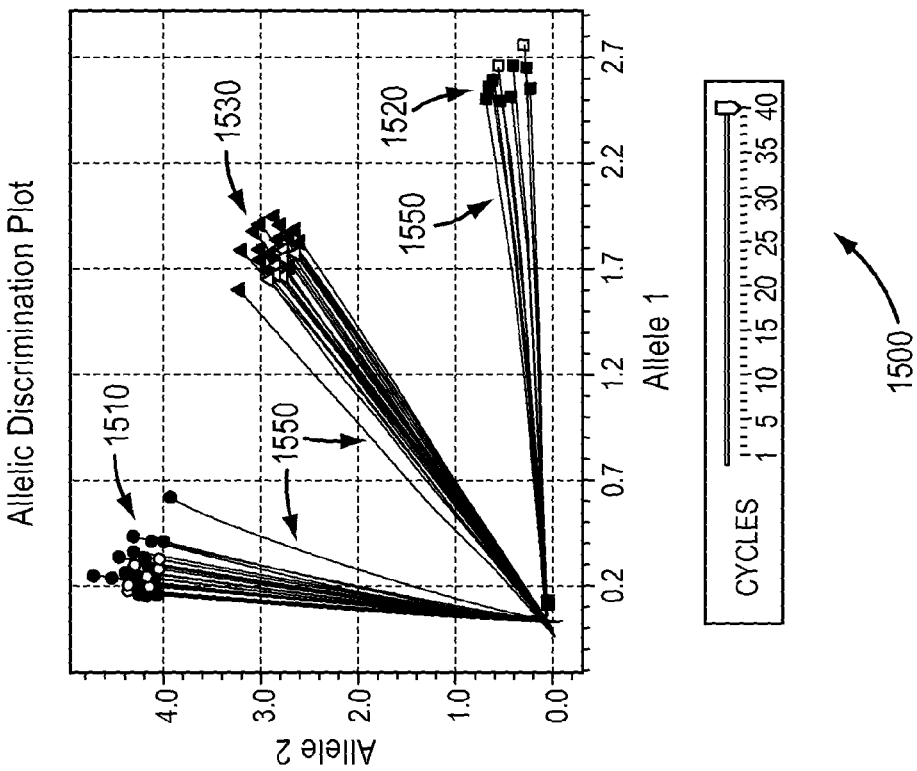

For example, in FIGS. 13A-13C, the data for a plurality of samples analyzed in a genotyping experiment are displayed. In FIG. 13A, three populations of samples 1310, 1320, and 1330, representing clusters of samples for homozygous (2/2), homozygous (1/1), and heterozygous (½), respectively. One of ordinary skill in the art will recognize a sample table representing an assay format for analyzing as many as 384 samples, where each sample is represented in a cell in an alpha-numeric designation for rows and columns. As can be seen from the sample table, there are 91 samples analyzed (U=unknown), 2 non-template controls (N), and three positive controls for the target gene being analyzed (1/1, 2/2, and ½). In FIG. 13B, an end user may select a particular group of samples, and have them highlighted for view and analysis on the plot. In FIG. 13C, an end user may select a region of particular interest on the sample table, and the associated samples are displayed on the plot. In various embodiments, an end user can scroll over the sample table and view the information associated with each sample (not shown) In this fashion, a ready analysis of conditions impacting genotyping results may be imparted to an end user.

According to various embodiments of systems and methods of the present teachings, the qPCR data sets taken over the course of the entire run time of a genotyping assay provide snap-shots over time of the progress of each sample in a plurality of samples. In various embodiments of systems and methods of the present teachings, a visualization tool presented in response to input from an end user may provide for a step-wise display of genotyping data, or it may provide for the display run as a video. In various embodiments according to the present teachings, such a visualization tool may provide an end user a dynamic review of all data as a function of time as an aid to analysis of genotyping data.

Figure 14A:
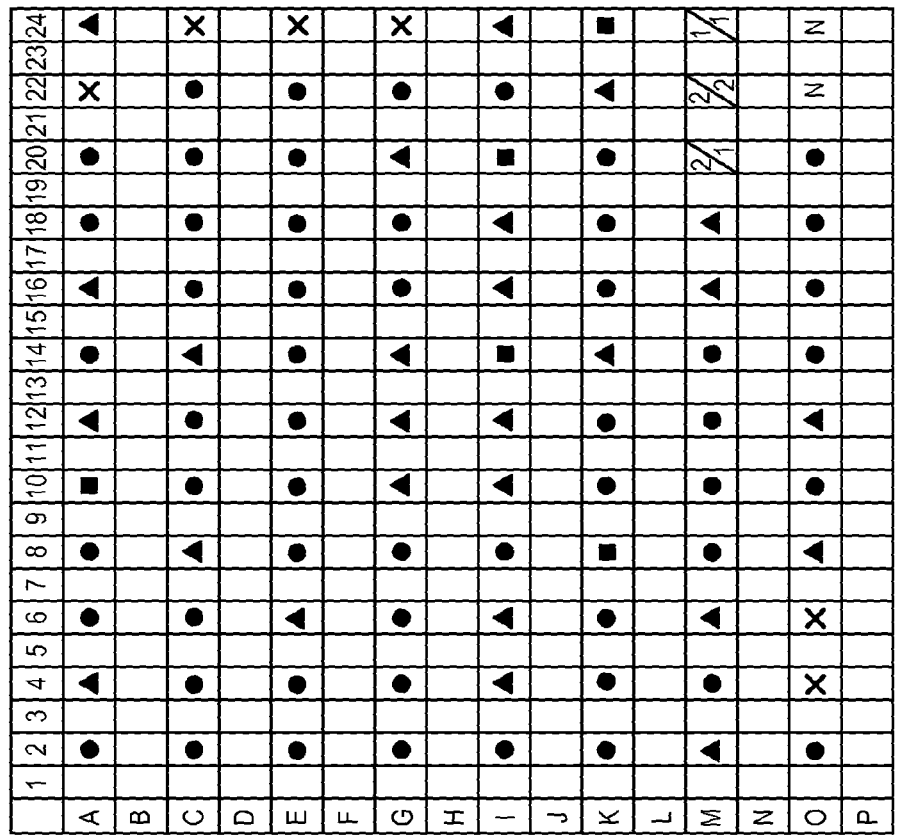
FIGS. 14A-14C display the interactive nature of an exemplary user interface, according to various embodiments of the present teachings.
Figure 14A:
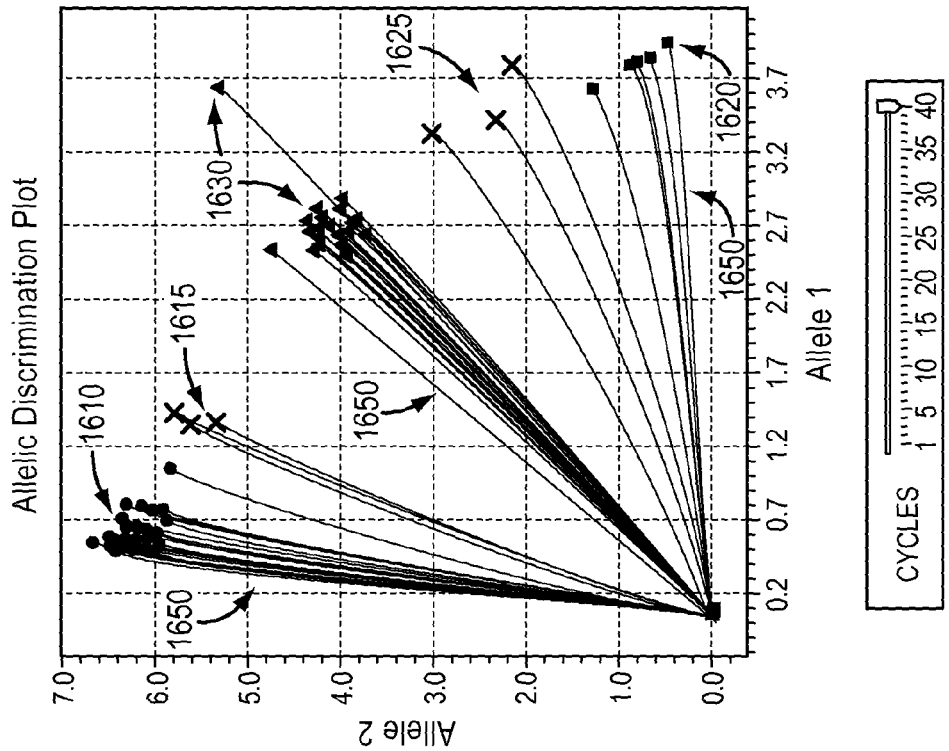
Figure 14B:
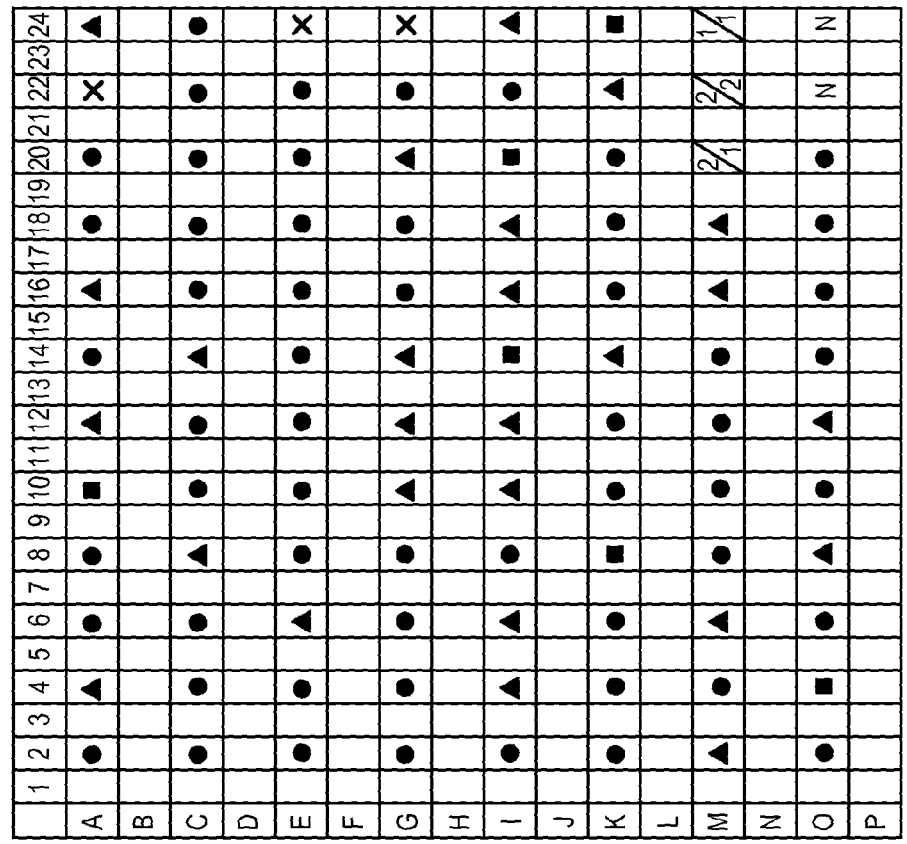
Figure 14B:
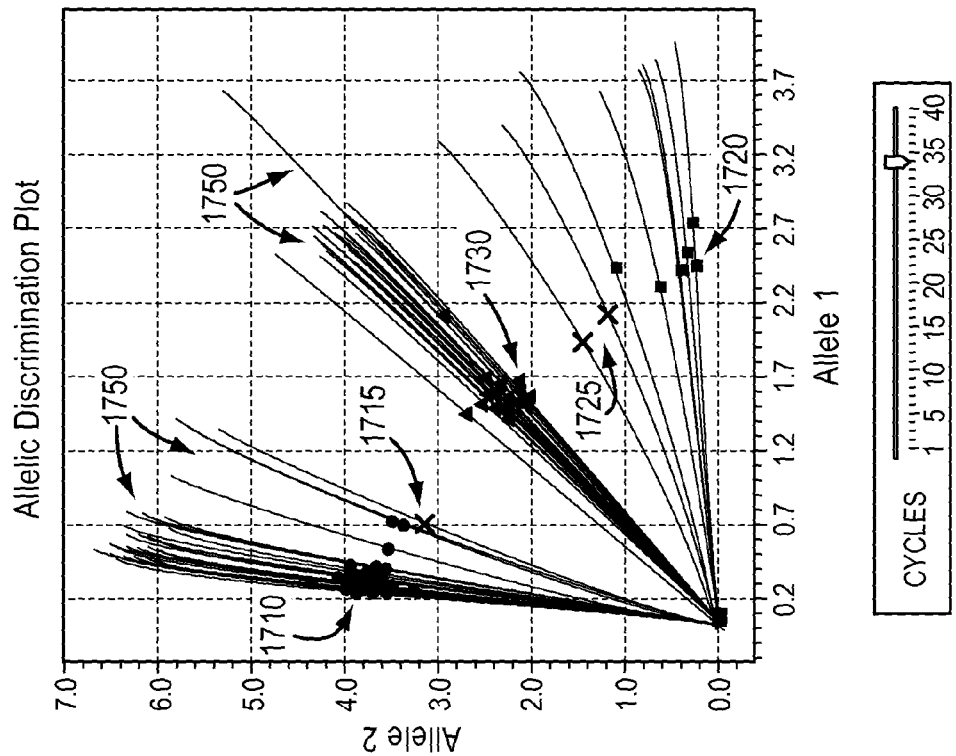
Figure 14C:
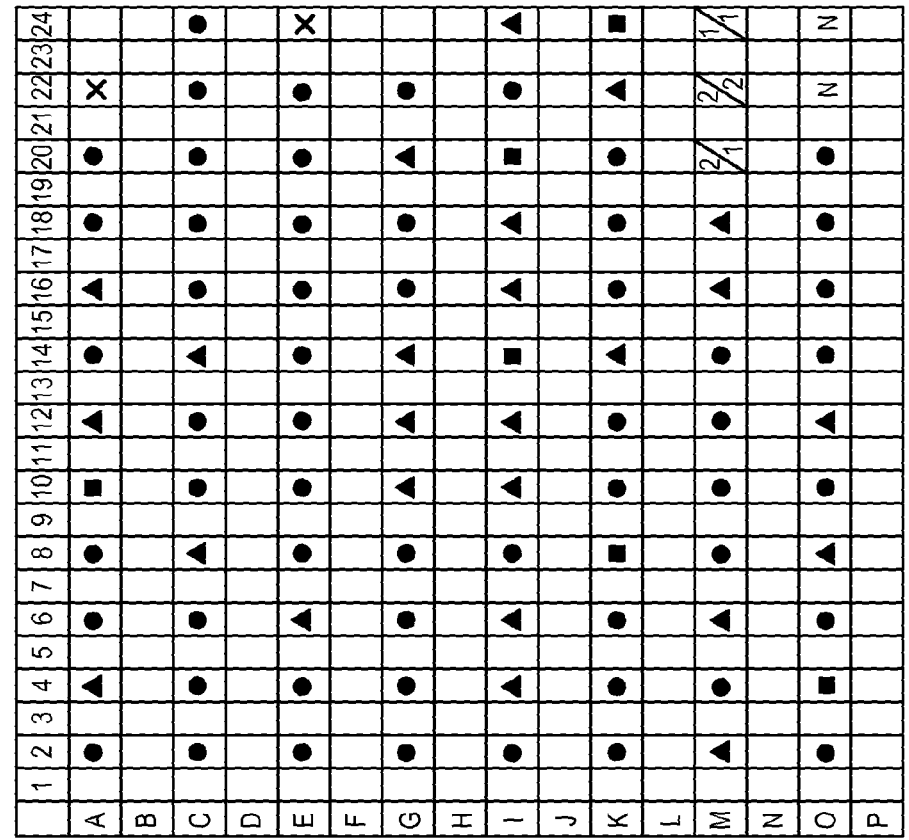
Figure 14C:
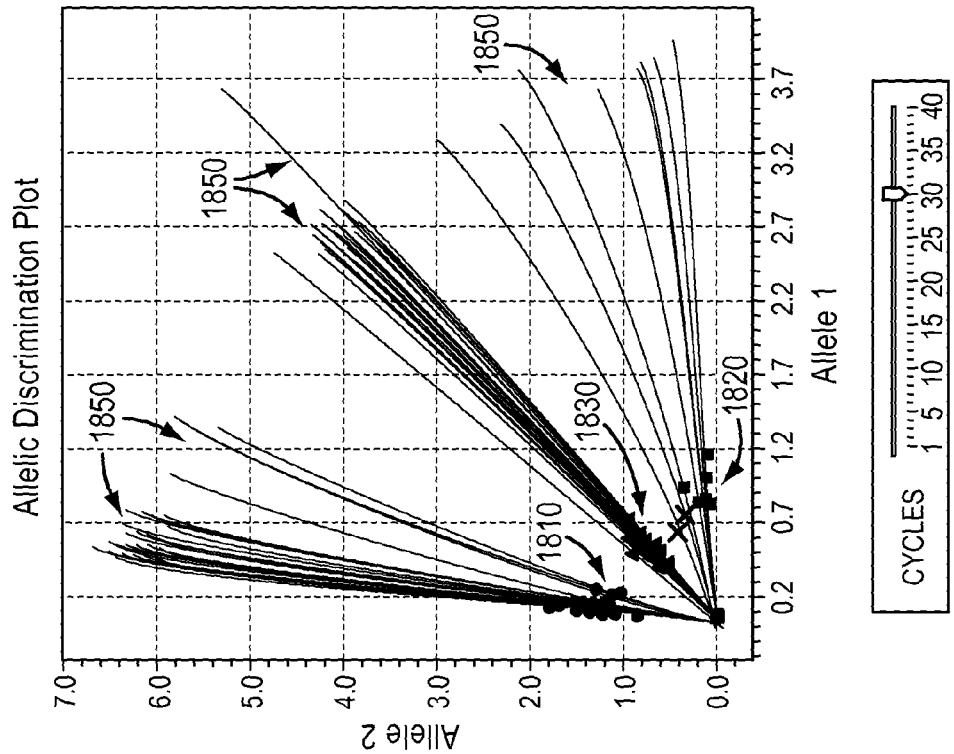

For example, FIG. 14A represents an analysis done in which three cluster of data 1610, 1620, and 1630, have been clearly called. However, clusters 1615 and 1625 have not been called by an algorithm used to analyze genotyping data, representing 6 uncalled samples in the set at end point. As displayed in FIG. 14B, an end user may select a time, represented for convenience to an end user as cycle number, to look at the status of the samples at a time earlier than the end-point time. As can be seen by inspection of FIG. 14B, at cycle 34, the number of samples for which no call can be made with confidence by a genotyping algorithm has dropped to three uncalled samples in the set of samples. Finally, in FIG. 14C, at 30 cycles, the number of uncalled samples has dropped to two samples. While for the purpose of explanation, FIGS. 14A-14C were presented in a reverse time sequence, according to various embodiments of systems and methods according to the present teachings, an end user may select any time slice of the progress of a genotyping assay for a plurality of samples in any order. Additionally, one of ordinary skill in the art will appreciate that while these data are exemplary of improving outcome by selecting a time represented by less than 40 cycles, analysis outcome may be also be enhanced in certain instances for a plurality of samples run for a greater number of cycles. For example for a gene target in a rare or damaged sample, an end user may select a protocol for greater than 40 cycles. In such a case, all the data is available to analyze using various embodiments of a visualization tool according to the present teachings.

The various implementations of the present teachings have been presented for purposes of illustration and description. They are not exhaustive and do not limit the present teachings to the precise form disclosed. On the contrary, the present teachings encompass various alternatives, modifications, and equivalents, as will be appreciated by those skilled in the art. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed:

1. A non-transitory computer-readable storage medium encoded with instructions, executable by a processor, for a visualization tool for genotyping data, the instructions comprising:
  providing instructions for a thermal cycling instrument to perform a full thermal cycle run;
  receiving by the processor a first data set at a first time for a sample during the run, wherein the first data set comprises a first intensity signal for a first probe and a first intensity signal for a second probe;
  receiving by the processor a second data set at a second time for the sample during the run, wherein the second data set comprises a second intensity signal for the first probe and a second intensity signal for the second probe;
  presenting an end user with a visualization tool, wherein the visualization tool provides a display of the data selected from:
    generating by the processor a first plot from the first data set and displaying the first plot, wherein the display provides a first confidence value for the first data set; and;
    generating by the processor a second plot from the second data set and displaying the second plot, wherein the display provides a second confidence value for the second data set; and
    stopping the thermal cycle run and calling the genotype before run completion when confidence values exceed a defined threshold.

2. The computer-readable storage medium of claim 1, wherein the selection of the dynamic display of the data is in response to input from the end user.

3. The computer-readable storage medium of claim 2, wherein the input from the end user is a step-wise selection of the display of the data.

4. The computer-readable storage medium of claim 2, wherein the input from the end user is a selection of a video display of the data.

5. The computer-readable storage medium of claim 1, wherein the processor receives the first data set and the second data set during thermal cycling.

6. The computer-readable storage medium claim 1, wherein the display comprises trajectory lines between the first data set and the second data set.

7. A computer implemented method for a visualization tool for genotyping data, the method comprising:
  providing instructions for a thermal cycling instrument to perform a full thermal cycle run;
  receiving by a processor a first data set at a first time for a sample during the run, wherein the first data set comprises a first intensity signal for a first probe and a first intensity signal for a second probe;
  receiving by a processor a second data set at a second time for the sample during the run, wherein the second data set comprises a second intensity signal for the first probe and a second intensity signal for the second probe;
  processing the data set on a computer to analyze genotyping data, the processing comprising:
    presenting an end user with a visualization tool, wherein the visualization tool provides a display of the data selected from:
      generating by the processor a first plot from the first data set and displaying the first plot, wherein the display provides a first confidence value for the first data set; and;

generating by the processor a second plot from the second data set and displaying the second plot, wherein the display provides a second confidence value for the second data set; and stopping the thermal cycle run and calling the genotype before run completion when confidence values exceed a defined threshold.

8. The computer implemented method of claim 7, wherein the selection of the dynamic display of the data is in response to input from the end user.

9. The computer implemented method of claim 8, wherein the input from the end user is a step-wise selection of the display of the data.

10. The computer implemented method of claim 8, wherein the input from the end user is a selection of a video display of the data.

11. The computer implemented method of claim 7, wherein the processor receives the first data set and the second data set during thermal cycling.

12. The computer implemented method of claim 7, wherein the display comprises trajectory lines between the first data set and the second data set.

13. A system comprising:
a processor; and
a memory in communication with the processor; the memory storing instructions for:
providing instructions for a thermal cycling instrument to perform a full thermal cycle run;
receiving by the processor a first data set at a first time for a sample during the run, wherein the first data set comprises a first intensity signal for a first probe and a first intensity signal for a second probe;
receiving by the processor a second data set at a second time for the sample during the run, wherein the second data set comprises a second intensity signal for the first probe and a second intensity signal for the second probe;
presenting an end user with a visualization tool, wherein the visualization tool provides a display of the data selected from:
generating by the processor a first plot from the first data set and displaying the first plot, wherein the display provides a first confidence value for the first data set; and
generating by the processor a second plot from the second data set and displaying the second plot, wherein the display provides a second confidence value for the second data set;
and;
stopping the thermal cycle run and calling the genotype before run completion when confidence values exceed a defined threshold.

14. The system of claim 13, wherein the selection of the dynamic display of the data is in response to input from the end user.

15. The system of claim 14, wherein the input from the end user is a step-wise selection of the display of the data.

16. The system of claim 14, wherein the input from the end user is a selection of a video display of the data.

* * * * *